(12) United States Patent
DeCourcy et al.

(10) Patent No.: US 10,286,374 B2
(45) Date of Patent: *May 14, 2019

(54) SHELL AND TUBE OXIDATION REACTOR WITH IMPROVED RESISTANCE TO FOULING

(71) Applicant: Arkema Inc., King of Prussia, PA (US)

(72) Inventors: Michael S. DeCourcy, Houston, TX (US); John L. Steinbach, League City, TX (US); Nicolas Dupont, Saint Avold (FR); Roger L. Roundy, Rosharon, TX (US)

(73) Assignee: Arkema Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/825,311

(22) Filed: Nov. 29, 2017

(65) Prior Publication Data

US 2018/0078919 A1 Mar. 22, 2018

Related U.S. Application Data

(62) Division of application No. 15/196,288, filed on Jun. 29, 2016, now Pat. No. 9,861,948, which is a division
(Continued)

(51) Int. Cl.
*B01J 8/06* (2006.01)
*C07C 51/235* (2006.01)
(Continued)

(52) U.S. Cl.
CPC ............. *B01J 8/067* (2013.01); *B01J 8/0453* (2013.01); *B01J 8/065* (2013.01); *B01J 15/005* (2013.01); *B01J 19/0046* (2013.01); *B01J 19/242* (2013.01); *C07C 51/215* (2013.01); *C07C 51/235* (2013.01); *C07C 51/252* (2013.01); *B01J 8/048* (2013.01); *B01J 2208/0092* (2013.01); *B01J 2208/00221* (2013.01); *B01J 2208/00849* (2013.01); *B01J 2208/025* (2013.01); *B01J 2219/0059* (2013.01);
(Continued)

(58) Field of Classification Search
CPC . B01J 8/0453; B01J 8/048; B01J 8/065; B01J 8/067; B01J 2208/00221; B01J 2208/00238; B01J 2208/00849; B01J 2208/0092; B01J 2208/025
See application file for complete search history.

(56) References Cited

U.S. PATENT DOCUMENTS 3,876,693 A 4/1975 Erpenbach et al.
4,029,636 A 6/1977 Lowry et al.
(Continued)

*Primary Examiner* — Lessanework Seifu
(74) *Attorney, Agent, or Firm* — Lynn B. Morreale

(57) ABSTRACT

The present disclosure relates to a single shell open interstage reactor ("SSOI"). The SSOI comprises a first reaction stage, an interstage heat exchanger, an open interstage region, and a second reaction stage. The SSOI may be configured for upflow or downflow operation. Further, the open interstage region of the SSOI may comprise a supplemental oxidant feed. When the open interstage region comprises a supplemental oxidant feed, the SSOI may further comprise a supplemental oxidant mixing assembly. Processes for producing acrylic acid through the oxidation of propylene are also disclosed.

33 Claims, 11 Drawing Sheets

Related U.S. Application Data of application No. 13/652,522, filed on Oct. 16, 2012, now Pat. No. 9,440,903.

(60) Provisional application No. 61/704,636, filed on Sep. 24, 2012.

(51) Int. Cl.
  *B01J 8/04*      (2006.01)
  *C07C 51/215*    (2006.01)
  *C07C 51/25*     (2006.01)
  *B01J 15/00*     (2006.01)
  *B01J 19/00*     (2006.01)
  *B01J 19/24*     (2006.01)

(52) U.S. Cl.
  CPC .......... *B01J 2219/0072* (2013.01); *B01J 2219/00479* (2013.01); *B01J 2219/00495* (2013.01); *B01J 2219/00594* (2013.01); *B01J 2219/30226* (2013.01); *B01J 2219/30265* (2013.01); *B01J 2219/30475* (2013.01)

(56) References Cited

U.S. PATENT DOCUMENTS

| | | |
|---|---|---|
| 4,147,885 A | 4/1979 | Shimizu et al. |
| 4,201,736 A | 5/1980 | Ellis et al. |
| 4,518,574 A | 5/1985 | Osman et al. |
| 4,873,368 A | 10/1989 | Kodowaki et al. |
| 5,426,221 A | 6/1995 | Willersinn |
| 6,069,271 A | 5/2000 | Tanimoto et al. |
| 6,384,274 B1 | 5/2002 | Elder et al. |
| 6,605,187 B1 | 8/2003 | Nonomura et al. |
| 6,624,315 B2 * | 9/2003 | Zehner ............ B01J 8/0285 549/256 |
| 6,639,106 B1 | 10/2003 | Elder et al. |
| 6,998,505 B2 | 2/2006 | Yada et al. |
| 7,038,079 B2 | 5/2006 | Hirao et al. |
| 7,226,567 B1 | 6/2007 | Olbert et al. |
| 7,491,368 B2 * | 2/2009 | Vogel ............ B01J 8/008 29/727 |
| 7,880,034 B2 | 2/2011 | Dubois |
| 7,897,813 B2 | 3/2011 | Tanimoto et al. |
| 7,906,679 B2 | 3/2011 | Aldrett-Lee et al. |
| 8,242,308 B2 | 8/2012 | Ho et al. |
| 8,524,787 B2 * | 9/2013 | Ermolaev ............ B01J 8/067 422/201 |
| 8,530,700 B2 | 9/2013 | Ho et al. |
| 2006/0099131 A1 | 5/2006 | Singh et al. |
| 2008/0021242 A1 | 1/2008 | Tanimoto et al. |
| 2009/0112367 A1 | 4/2009 | DeCourcy et al. |
| 2009/0253934 A1 | 10/2009 | Ho et al. |
| 2010/0015017 A1 | 1/2010 | Ha et al. |

* cited by examiner

SHELL AND TUBE OXIDATION REACTOR WITH IMPROVED RESISTANCE TO FOULING

CROSS REFERENCE TO RELATED APPLICATION

This application claims priority to U.S. application Ser. No. 15/196,288, filed Jun. 29, 2016, which claims priority to U.S. application Ser. No. 13/652,522, filed Oct. 16, 2012, now granted U.S. Pat. No. 9,440,903, which claims priority to U.S. Provisional Application No. 61/704,636 filed Sep. 24, 2012.

FIELD OF THE INVENTION

The invention pertains to shell and tube oxidation reactors and processes for making acrylic acid through the oxidation of propylene.

DISCUSSION OF THE RELATED ART

The production of acrylic acid by fixed-bed catalytic oxidation of propylene is widely practiced and involves oxidizing propylene to the intermediate acrolein and then further oxidizing acrolein to acrylic acid. Numerous solid particulate-type catalysts have been developed to facilitate this two-stage oxidation process and methods for preparing these catalysts are well documented in the literature.

In general, commercial-scale manufacturing facilities utilize two compositionally distinct catalysts, a first stage catalyst and a second stage catalyst, in the production of acrylic acid. First stage catalysts (referred to herein as "R1 catalysts") are mixed metal oxide ("MMO") catalysts generally comprising molybdenum, bismuth, and optionally iron, and are used to promote the conversion of propylene to acrolein. Second stage catalysts (referred to herein as "R2 catalysts") are also mixed metal oxide (MMO) catalysts, but these generally comprise molybdenum and vanadium, and are used to promote the conversion of acrolein to acrylic acid.

Current commercial-scale processes for the production of acrylic acid often utilize reactors modeled on shell-and-tube heat exchangers. Typically, such commercial reactors comprise from about 12,000 up to about 22,000 tubes in a single reaction vessel and may have acrylic acid production capacities of up to 100 kT/year (220,000,000 pounds/year) operating with a 93% onstream factor. Large-scale commercial reactors, though less common, may comprise 25,000 up to about 50,000 tubes in a single reaction vessel, with production capacities of up to 225 kT/year (500,000,000 pounds/year). In such shell-and-tube type reactors, a fixed catalyst bed can be assembled by loading particulate-type MMO catalysts into the tubes of the reactor. Process gases may flow through the tubes, in direct contact with the catalyst particles, while coolant can be passed through the vessel shell to remove the heat of reaction. Typical coolants include molten nitrate salts and organic heat transfer fluids, such as Dowtherm™. The resulting product gas from the reactor can be collected and purified in additional downstream equipment, such as one or more of quench vessels, absorber columns, dehydration columns, extractors, azeotropic distillation towers, and crystallizers, to obtain acrylic acid product suitable for sale, or for use in the production of acrylate esters, superabsorbent polymers, or the like.

There are two basic shell-and-tube type oxidation reactor designs commonly used in the prior art: tandem reactors and single reactor shell ("SRS") reactors.

Tandem reactors generally comprise two separate shell-and-tube type reaction vessels connected in series by an intermediate conduit. The two reaction vessels are operated in series, such that the conversion of propylene to acrolein can be performed in the first reaction vessel (using an R1 catalyst) and the conversion of acrolein to acrylic acid can be performed in the second reaction vessel (using an R2 catalyst). Each reaction vessel shell can be supplied with its own circulation of coolant such that the operating temperatures of the first reaction vessel and the second reaction vessel may be controlled independent of each other. Representative examples of tandem reactors are provided in U.S. Pat. Nos. 4,147,885; 4,873,368; and 6,639,106. In some embodiments, an optional heat exchanger may be added between the first reaction vessel and the second reaction vessel to cool the intermediate process gas stream before it enters the second reaction vessel. In other embodiments, the tandem reactor design may incorporate "supplemental oxidant feed" capability, wherein additional oxygen (or air) is provided to the second reaction vessel through a connection on the intermediate conduit; such a feature may allow the tandem reactor to be operated at a higher production rate and/or lower the oxygen concentration in the reactor feed, thereby reducing the potential for feed system fires (see for example U.S. Pat. No. 7,038,079). Despite many years of development and optimization, however, auto-oxidation of acrolein, organic fouling of the intermediate conduit, and the high capital cost associated with having two reaction vessels (vs. one) remain major drawbacks of tandem reactors.

SRS reactors typically comprise a single shell-and-tube type reaction vessel with tubes that are approximately twice as long as the tubes within a Tandem reaction vessel. The upstream end of each tube can be loaded with R1 catalyst and the downstream end of each tube can be loaded with R2 catalyst, forming two sequential reaction zones within each tube. A quantity of inert material—such as raschig rings—may be placed at approximately the midpoint of each tube, forming a so-called inert substance layer, which separates the two catalytic reaction zones from each other. Additionally, an intermediate tubesheet may be placed within the shell of the SRS reactor, roughly coincident with the inert substance layer, to divide the shell into upper and lower cooling zones. Each cooling zone can be supplied with its own circulation of coolant such that the operating temperatures of the first reaction zone and the second reaction zone may be controlled independent of each other. Representative examples of SRS reactors are provided in U.S. Pat. Nos. 6,069,271 and 6,384,274. Although auto-oxidation of acrolein can be largely eliminated in the SRS reactor, accumulation of molybdenum and carbonaceous materials within both the interstage zone and the second reaction zone remains a significant problem; these accumulations not only restrict flow through the reaction tubes, thereby limiting productivity, but they also reduce yield, due to masking of the catalytic surface in the R2 reaction zone. Additionally, the long tubes utilized in the SRS reactor design make it very difficult to remove accumulated solids from the midpoint of the tubes, requiring the use of aggressive techniques, such as high pressure waterblasting and the use of drilling-devices, such as the apparatus disclosed in published U.S. Patent Application Publication No. US 2009/0112367. Another drawback of the SRS reactor design is that it cannot be easily modified to accommodate supplemental oxidant feed.

BRIEF SUMMARY OF THE INVENTION

One aspect of the invention provides a single shell open interstage ("SSOI") reactor comprising a shell-and-tube type reactor design which addresses at least some of the shortcomings of the prior art tandem reactors and SRS reactors while economically producing commercial quantities of acrylic acid. The SSOI reactor of the invention may provide at least one or more of the following advantages as compared to known shell-and-tube reactors: lower capital costs by using a single reaction vessel, enhanced accessibility during cleaning and catalyst replacement, decreased carbonaceous solids and molybdenum oxides accumulation within the reactor, decreased pressure drop across the reactor, decreased downtime required for decoking, decreased loss of catalytic activity due to solids deposition, decreased auto-oxidation of acrolein, decreased byproduct acetic acid formation, decreased partial catalyst repacks through matching of catalyst useful life, and the ability to provide supplemental oxidant between reaction stages.

One aspect of the invention relates to an upflow single shell open interstage reactor comprising:
a) a first shell-and-tube reaction stage comprising a plurality of reaction tubes, wherein the reaction tubes of the first reaction stage comprise a first catalyst;
b) an interstage heat exchanger;
c) an open interstage region; and
d) a second shell-and-tube reaction stage comprising a plurality of reaction tubes, wherein the reaction tubes of the second reaction stage comprise a second catalyst;
wherein said interstage heat exchanger is positioned between said first reaction stage and said open interstage region, and wherein said reactor is configured for upflow operation.

Another aspect of the invention relates to a single shell open interstage stage reactor, comprising, in process-flow order:
a) a shell-and-tube first reaction stage comprising a plurality of reaction tubes containing a first catalyst;
b) an integrated interstage heat exchanger comprising a plurality of tubes coaxially continuous with the plurality of reaction tubes of the first reaction stage;
c) an open interstage region comprising a supplemental oxidant mixing assembly; and
d) a shell-and-tube second reaction stage comprising a plurality of reaction tubes containing a second catalyst.

Yet another aspect of the invention relates to a single shell open interstage reactor comprising:
a) a first shell-and-tube reaction stage comprising a plurality of reaction tubes;
b) an interstage heat exchanger;
c) an open interstage region; and
d) a second shell-and-tube reaction stage comprising a plurality of reaction tubes;
wherein the reaction tubes of the second reaction stage have a diameter greater than a diameter of the reaction tubes of said first reaction stage.

Other further aspects of the invention relate to methods of making acrylic acid using the reactors disclosed herein.

Further aspects of the invention relate to a single shell open interstage reactor for producing acrylic acid from propylene comprising, in process-flow order:

a) a first shell-and-tube reaction stage comprising a plurality of reaction tubes, wherein the reaction tubes of the first reaction stage comprise a first catalyst for oxidizing propylene to produce acrolein;
b) an interstage heat exchanger;
c) an open interstage region; and
d) a second shell- and tube reaction stage comprising a plurality of reaction tubes, wherein the reaction tubes of the second reaction stage comprise a second catalyst for oxidizing acrolein to produce acrylic acid; and wherein the reaction tubes of the second reaction stage have a diameter greater than 22.3 mm (0.878 in).

Still further aspects of the invention relate to a process of making acrylic acid comprising:
a) providing a mixed feed gas comprising propylene to a first reaction stage located at a lower end of a single shell open interstage reactor, wherein the first reaction stage comprises a mixed metal oxide catalyst;
b) oxidizing the propylene in the first reaction stage to produce a process gas comprising acrolein;
c) cooling the process gas in an interstage heat exchanger;
d) passing the cooled process gas upward through an open interstage region;
e) passing the process gas upward to a second reaction stage, wherein the second reaction stage comprises a mixed metal oxide catalyst; and
f) oxidizing the acrolein in the second reaction stage to produce a product gas comprising acrylic acid.

DETAILED DESCRIPTION

Figure 1A:
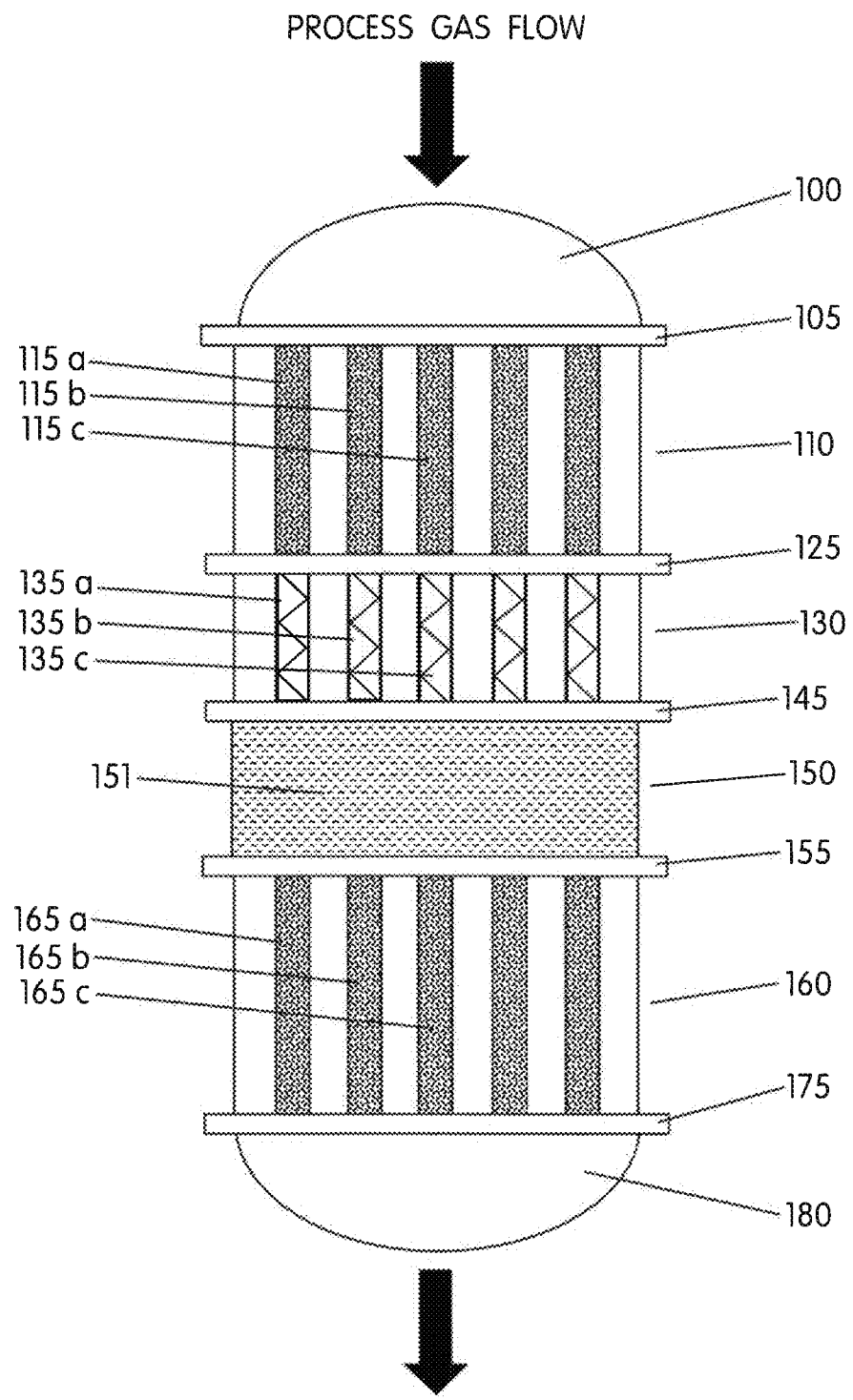
FIG. 1a is a side view representing the tubeside (process) features for a first embodiment of an SSOI reactor.

It is to be understood that both the foregoing general description and the following detailed description are exemplary and explanatory only and are not restrictive of the present teachings. All patents and patent applications cited in this application are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, dimensions, flow rates, concentrations, times, etc. discussed in the present teachings, such that slight and insubstantial deviations are within the scope of the present teachings.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, shell-and-tube reactor design, acrylic acid production, and oxidation reactions, are those well known and commonly used in the art. As utilized in accordance with the embodiments provided herein, the following terms, unless otherwise indicated, shall be understood to have the following meanings:

As used herein, the phrase "interstage heat exchanger" or "ISHX" refers to a heat exchanger located between stages of a single reactor. For example, the ISHX may be positioned between a first reaction stage and a second reaction stage.

The phrase "integrated interstage heat exchanger," or "integrated ISHX," refers to a heat exchanger having tubes that are coaxially continuous with the reaction tubes of a reaction stage.

The phrase "open interstage" or "OIS" refers to region comprising no reaction tubes and located between stages of a single reactor or between a stage and an interstage heat exchanger of a single reactor. For example, the OIS may be positioned between an interstage heat exchanger and a second reaction stage.

As used herein, the phrase "high surface area material," and variations thereof, refers to a surface area to bulk volume ratio of at least 78.7 $m^2/m^3$ (24 $ft^2/ft^3$).

As used herein, the term "inert material" means a material which is substantially ineffective at catalyzing a reaction of the feed materials or reaction products. For example, in a reactor producing acrylic acid through the oxidation of propylene, an inert material is one which is substantially ineffective at catalyzing the oxidation of propylene or of catalyzing the oxidation of acrolein.

The term "stable material," as used herein, refers to materials which do not deform, melt, vaporize, decompose, or combust when exposed to process temperatures, process operating pressures, or chemical components within the process.

As used herein, the term "interface" refers to the boundary between two adjacent reactor sections. The term "connection" refers to the point of circumferential contact between adjacent reactor sections at an interface and may be temporary or permanent. The term "tubesheet" refers to a planar surface positioned at an interface, said surface extending over substantially the entire cross-section of the reactor and comprising a plurality of holes through which the ends of the reaction tubes pass. The ends of the reaction tubes are attached to the tubesheet by known means such as welding or rolling, and the tubesheet is further attached at its outer circumference to the vessel shell, thereby preventing shell side coolant from passing from one section to another. The term "interstage baffle" refers to a planar surface positioned at an interface, said surface extending over substantially the entire reactor cross-section and comprising a plurality of holes through which the reaction tubes pass. Unlike a tubesheet, however, the reaction tubes are not attached to the baffle, and fluidic communication of shell side coolant is allowed between adjacent sections. Finally, the term "segmental baffle" refers to a planar surface NOT positioned at an interface, said surface extending over only a portion of the reactor cross-section and comprising a plurality of holes through which the reaction tubes pass. As with an interstage baffle, the reaction tubes are not attached to a segmental baffle, and fluidic communication of shell side coolant is allowed between opposite surfaces of the segmental baffle.

The terms "diameter" and "cross-sectional area," when referring to a tube, are used to define the size of the tube rather than the shape of the tube. The examples provided herein use tubes having a circular cross-section, but tubes having other shapes may be used. For tubes having other shapes, one of ordinary skill in the art would understand that the diameters disclosed herein can be converted to the appropriate dimension for alternative shapes by determining the cross-sectional area while taking into account any variations (e.g., heat transfer, mass transfer, etc.) resulting from the alternative shape. The terms "diameter" and "cross-sectional area" are used to refer to the diameter or cross-sectional area of the opening of the tube, i.e., the interior diameter or cross-sectional area.

As used herein, the terms "upflow" and "downflow" relate to the direction of flow through the reactor with respect to gravitational force. Upflow describes a upward vertical process flow that proceeds against the gravitational force. Downflow describes a downward process flow that proceeds in the direction of gravitational force.

The term "residence time" refers to the amount of time gas spends in one or more specified sections. For example, the residence time may refer to the amount of time spent in the ISHX. Similarly, the residence time may refer to the amount of time spent in multiple sections, such as, for example, the combined amount of time spent in the ISHX and OIS region. Unless otherwise specified, the residence time of process gas flow within the reactor is determined at the reference conditions of 240° C. and 30 psia (2 atm) pressure.

In at least one embodiment, the SSOI reactor comprises, in process-flow order:
   a) an inlet reactor head;
   b) a shell-and-tube first reaction stage;
   c) an integrated interstage heat exchanger;
   d) an open interstage region;
   e) a shell-and-tube second reaction stage; and
   f) an outlet reactor head.

The first reaction stage ("R1") may comprise a plurality of reaction tubes, each of which may be filled with a catalyst, e.g., an R1 catalyst. When used for the oxidation of propylene to form acrylic acid, the R1 catalyst may be a MMO catalyst chosen from oxides of molybdenum, bismuth, and iron.

The first reaction stage may comprise a shellside coolant. One of ordinary skill in the art would appreciate that the coolant and coolant circulation can be selected and designed to meet the heat transfer needs of the specific application.

The second reaction stage ("R2") may comprise a plurality of reaction tubes. The R2 reaction tubes may be filled with a catalyst (an R2 catalyst) to catalyze the second stage reaction. In the exemplary reaction, where acrolein is oxidized in R2 to form acrylic acid, the R2 catalyst may comprise an MMO chosen from molybdenum and vanadium oxides. The shellside of the second reaction stage may comprise a coolant. The coolant of the second reaction stage may be controlled independently of the coolant of the first reaction stage. Alternatively, the coolant of the second reaction stage may be controlled with the coolant of the first reaction stage.

In at least one embodiment, the ISHX may comprise a shellside coolant. The ISHX coolant may be controlled separately or together with the first reaction stage coolant. In at least one embodiment, the ISHX coolant is controlled independently of the first reaction stage coolant. In accordance with at least one embodiment, the ISHX coolant maintains the temperature of the process gas leaving the ISHX between 240° C. and 280° C.

In at least one embodiment of the present disclosure, the R1 and R2 reaction tubes can have a different diameter or cross-sectional area. For example, the R2 reaction tubes may be larger than the R1 reaction tubes. Alternatively, the R1 and R2 reaction tubes may have the same diameter or cross-sectional area. In at least one embodiment, the R2 reaction tubes may have a cross-sectional area at least 25% greater than the cross-sectional area of the R1 reaction tubes. In a further embodiment, the R2 reaction tubes may have a cross-sectional area at least 50% greater than the cross-sectional area of the R1 reaction tubes.

In at least one embodiment, the R1 reaction tubes may have a diameter of 22.3 mm (0.878 in) or less. In other embodiments, the R1 reaction tubes may have a diameter greater than 22.3 mm (0.878 in), such as, for example, 25.4 mm (1 in) or more.

In at least one embodiment, the internal diameter of the tubes of second reaction stage within the SSOI reactor can be greater than 22.3 mm. In at least one embodiment, the R1 and R2 reaction tubes have a diameter greater than 22.3 mm (0.878 in). In a further embodiment the internal diameter of the tubes of second reaction stage within the SSOI reactor range from 23.6 mm to 50 mm. In at least one embodiment, the internal diameter of the tubes of second reaction stage within the SSOI reactor is at least 25.4 mm (1 in). In accordance with an embodiment of the present disclosure, the tubes of the second reaction stage are not more than 4,500 mm (177 in) in length.

The negative impact on heat removal of larger diameter tubes may be compensated for with appropriate adjustments in one or more of the other design variables, such as for example, the number of shellside baffles, the baffle geometry and placement, the tubesheet layout and spacing between tubes (also known as tube pitch), the circulation rate of the cooling salt, and the supply temperature of the cooling salt. For example, in one embodiment, low salt circulation rates through the reactor shell are employed, thereby minimizing power requirements for the salt circulation pumps; such a design philosophy may generally result in a temperature rise of the salt through the shell of the reactor (salt temperature out relative to salt temperature in) of as much as 14 to 17° C. (25 to 30° F.). In an alternative embodiment, high salt circulation rates are utilized and the temperature increase of the salt through the shell of the reactor is constrained to the range of just 1 to 3° C. (2-5° F.).

Such design adjustments can be made by one of ordinary skill in the art of heat exchanger design, using commercially available design software from HTRI or the like; alternatively, cooling system design services may be outsourced to established reactor fabrication companies such as, for example, MAN Turbo AG (formerly Deggendorfer Werft and Eisenbau GmbH), who will use their own well-established design rules and methodologies.

Similarly, the number of reaction tubes in R1 and R2 may be the same or different. In at least one embodiment, the number of R1 reaction tubes may be greater than the number of R2 reaction tubes. In at least one further embodiment, the number of R1 reaction tubes may be greater than the number of R2 reaction tubes, and the R2 reaction tubes may have a greater diameter or cross-sectional area than the R1 reaction tubes.

The SSOI reactors disclosed herein may be configured for upflow or downflow operation. In at least one embodiment, the SSOI reactors are configured for upflow operation. In an upflow SSOI reactor, the inlet reactor head is located at the bottom and the outlet reactor head is located at the top of the SSOI reactor.

In at least one embodiment, the OIS region comprises a supplemental oxidant supply. When the supplemental oxidant supply is present, the OIS region may further comprise a supplemental oxidant mixing assembly.

In embodiments wherein acrylic acid is produced from the oxidation of propylene, the combined residence time within both the ISHX and the OIS (known herein as the "interstage residence time") is 3 seconds or less. In at least one embodiment, the residence time within the ISHX is less than 1.5 seconds.

In at least one embodiment, the process gases of the operating SSOI reactor can be monitored for unreacted propylene concentration and unreacted acrolein concentration using at least one online analyzer, such as for example, one or more of a gas chromatograph, a near infrared ("NIR") analyzer, a tunable diode laser ("TDL") analyzer, or a Raman spectrograph, and the salt supply temperatures to the first reaction stage and the second reaction stage can be adjusted to control the conversions of propylene and of acrolein. In one embodiment, the supply temperature of the first stage cooling salt ($T_{R1salt}$) may be adjusted to maintain propylene conversion at 94% or greater, at 95% or greater, or at 96.5% or greater.

In another embodiment, the supply temperature of the first stage cooling salt ($T_{R1salt}$) can be adjusted to maintain the unreacted propylene concentration in the SSOI reactor product gas at between 0.05 and 0.35 mol %, such as, for example, between 0.13-0.26 mol %. In one embodiment, the supply temperature of the second stage cooling salt ($T_{R2salt}$) can be adjusted to maintain acrolein conversion at 98% or greater, such as at 99% or greater, or at 99.5% or greater.

In another embodiment, the supply temperature of the second stage cooling salt ($T_{R2salt}$) can be adjusted to maintain the unreacted acrolein concentration in the SSOI reactor product gas at not more than 500 ppm, such as, for example, not more than 300 ppm.

In at least one embodiment, temperature measurement devices, such as thermocouples or Resistance Thermal Devices (RTDs), can be provided within the reaction system to monitor process operating conditions and to optionally serve as sensors within safety instrumented systems (SIS) for the reaction system. Individual and multipoint E-type, J-type, and K-type thermocouples are all suitable for use with the SSOI reactor of the present invention and are commercially available from multiple suppliers, including STI manufacturing Inc. of Willis, Tex. USA; Watlow Electric Manufacturing Company of St. Louis, Mo. USA; Sandelius Instruments, Inc of Houston, Tex. USA, and Gayesco International Inc. of Pasadena, Tex. USA.

One or more thermocouples may be optionally placed within one or more of the inlet head, outlet head, inlet piping, outlet piping, and open interstage region. In one embodiment, a plurality of thermocouples may be placed within the reactor inlet head for use with a SIS shutdown system. According to at least one embodiment, at least 4 thermocouples may be installed within the open interstage region and these thermocouples may be evenly distributed throughout the interstage region. Further, thermocouples may be optionally attached directly to the tubesheets within the reactor.

A plurality of multipoint process thermocouples can be used within the tubes of the reactor to monitor process-side catalyst temperature at varying distances along the axis of the tube. In at least one embodiment, a plurality of multipoint salt thermocouples can be placed within the tubes of the reactor to monitor shellside salt temperature along the length of the reactor. It should be noted, however, that a multipoint process thermocouple and a multipoint salt thermocouple cannot coexist in the same reactor tube.

In one embodiment, a multipoint process thermocouple assembly, comprising 14 thermocouple junctions placed at varying intervals along its length, and housed within a 3.2 mm outside diameter sheath, is used within a first reaction stage tube of 22.3 mm internal diameter. In another embodiment, a multipoint process thermocouple assembly, comprising at least 10 thermocouple junctions placed at equal intervals along its length, and housed within a 6 mm outside diameter sheath, is used within a first reaction stage tube of 25.4 mm internal diameter. In either embodiment, the process thermocouple assembly can be oriented along the centerline of the reactor tube and the catalyst and inerts can be placed within the remaining annular space of the tube.

In at least one embodiment, at least 4 reactor tubes can be fitted with such multipoint process thermocouple assemblies, such as, for example, at least 6 tubes, or at least 10 tubes. Similarly, in one embodiment, a multipoint salt thermocouple assembly, comprising 4 thermocouple junctions placed at equal intervals along its length, and housed within a 3.2 mm outside diameter sheath, is used within a first reaction stage tube of 22.3 mm internal diameter.

In an alternative embodiment, a multipoint salt thermocouple assembly, comprising at least 3 thermocouple junctions placed at equal intervals along its length, and housed within a 6 mm outside diameter sheath, can be used within a first reaction stage tube of 25.4 mm internal diameter. At least 4 reactor tubes can be fitted with such multipoint salt thermocouple assemblies, such as, for example, at least 6 tubes, or at least 10 tubes. In one embodiment, the salt thermocouple assembly can be oriented along the centerline of the reactor tube, inert spheres are placed within the remaining annular space of the tube, and a sealable cap or plug is placed on at least the upstream end of the tube to prevent axial process gas flow through the tube. In an alternative embodiment, the salt thermocouple assembly can be oriented along the centerline of the reactor tube and small diameter (e.g., not more than 4 mm in diameter) inert particles, such as, for example, sand, alumina powder, or silicon carbide grit, can be placed within the remaining annular space of the tube to provide high resistance to axial process gas flow; such an embodiment may further optionally include a sealable cap or plug on at least the upstream end of the tube.

In one embodiment, a multipoint process thermocouple assembly, comprising at least 8 thermocouple junctions placed at varying intervals along its length, and housed within a 3.2 mm outside diameter sheath, can be used within a second reaction stage tube of 22.3 mm internal diameter. In another embodiment, a multipoint process thermocouple assembly, comprising at least 10 thermocouple junctions placed at equal intervals along its length, and housed within a 6 mm outside diameter sheath, can be used within a second reaction stage tube of 25.4 mm internal diameter. The process thermocouple assembly can be oriented along the centerline of the reactor tube and the catalyst and inerts can be placed within the remaining annular space of the tube. In at least one embodiment, at least 4 reactor tubes are fitted with such multipoint process thermocouple assemblies, such as, for example, at least 6 tubes, or at least 10 tubes. Similarly, in one embodiment, a multipoint salt thermocouple assembly, comprising at least 2 thermocouple junctions placed at equal intervals along its length, and housed within a 3.2 mm outside diameter sheath, can be used within a second reaction stage tube of 22.3 mm internal diameter.

In an alternative embodiment, a multipoint salt thermocouple assembly, comprising at least 3 thermocouple junctions placed at equal intervals along its length, and housed within a 6 mm outside diameter sheath, can be used within a second reaction stage tube of 25.4 mm internal diameter. In at least one embodiment, at least 4 reactor tubes can be fitted with such multipoint salt thermocouple assemblies, such as, for example, at least 6 tubes, or at least 10 tubes. In one embodiment, the salt thermocouple assembly can be oriented along the centerline of the reactor tube, inert spheres are placed within the remaining annular space of the tube, and a sealable cap or plug is placed on at least the upstream end of the tube to prevent axial process gas flow through the tube. In an alternative embodiment, the salt thermocouple assembly can be oriented along the centerline of the reactor tube and small diameter (e.g., not more than 4 mm in diameter) inert particles, such as, for example, sand, alumina powder, or silicon carbide grit, are placed within the remaining annular space of the tube to provide high resistance to axial process gas flow; such an embodiment may further optionally include a sealable cap or plug on at least the upstream end of the tube.

Figure 1B:
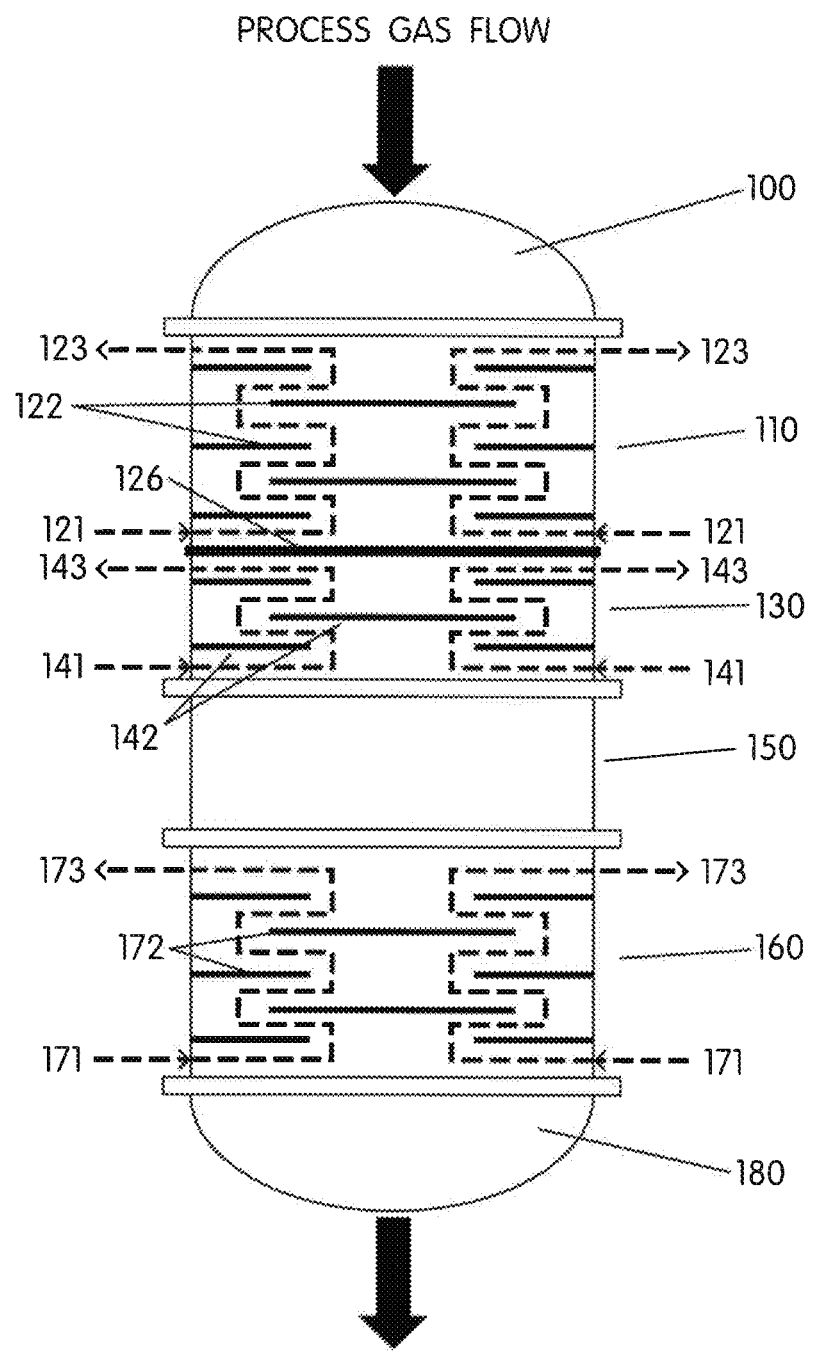
FIG. 1b is a side view representing the shellside (coolant) features for a first embodiment of an SSOI reactor.
Figure 1C:
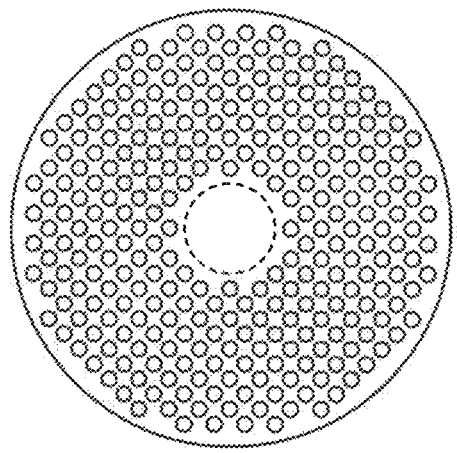
FIG. 1c is a top view representing the tubesheet layout for a first embodiment of an SSOI reactor.

FIGS. 1a, 1b, and 1c in combination represent one embodiment of a single shell open interstage ("SSOI") reactor design. The reactor of this embodiment has a shell diameter of about 5,600 mm (18.4 feet) and an overall length of more than 15,240 mm (50 feet). At typical feed ratios and total feed gas space velocity of 1770 $hr^{-1}$ (determined at 0° C. and 1 atm), the reactor of this embodiment has a nominal annual production capacity of about 100 kT of acrylic acid.

Feed gases (comprising, for example, propylene, steam, oxygen, and nitrogen) enter the reactor from the top (see FIG. 1a), flow vertically downward through the reactor, and exit the reactor at the bottom. This arrangement is therefore a downflow process configuration.

Major sections of the reactor include the inlet head 100, the first reaction stage 110 ("R1"), the interstage heat exchanger 130 ("ISHX"), the open interstage region 150, the second reaction stage 160 ("R2"), and the outlet head 180. Unless otherwise specified, all reactor components can be constructed of carbon steel, such as for example ASME SA-516 grade 70 carbon steel.

The interface between adjacent sections, identified in the figures as 105, 125, 145, 155, and 175, may comprise permanent (e.g., welded) connections or may optionally comprise separable connections, such as flanged connections secured with a plurality of fasteners, such as for example bolts or clamps. In the embodiment of FIG. 1a, interface 105 and 175 are separable connections, allowing inlet head 100 and outlet head 180 to be easily removed for catalyst replacement, while interfaces 125, 145 and 155 are welded connections.

In this embodiment, reactor inlet head 100 is constructed of 316 stainless steel for added corrosion resistance. Both reactor inlet head 100 and outlet head 180 also incorporate optional temperature control components (not shown), such as for example electric tracing, steam heating jackets, and circulating-salt heat transfer coils, for use in maintaining internal surface temperatures above the dewpoint temperature of the process gas stream. External insulation can also be employed on the reactor heads as well as elsewhere on the reactor shell and associated piping systems.

Reactor inlet head 100 and outlet head 180 may be further outfitted with one or more optional emergency pressure relief devices (not shown), such as, for example, pressure safety valves (PSVs) or rupture discs. In some embodiments, such emergency pressure relief devices may instead be installed on the inlet and/or outlet piping connected to the reactor.

Referring again to FIG. 1a, the first reaction stage 110 has a length of 4,600 mm (15 feet) and contains a plurality of seamless carbon steel tubes, represented generally in the figure as 115a, 115b, 115c. The entrance end of each tube in the first reaction stage can be attached, for example by welding or rolling, to the R1 inlet tubesheet (not shown per se, but located at the same position in the figure as separable connection 105). Each tube within the first reaction stage 110 extends through interstage baffle 126 (see FIG. 1b) and passes completely through the interstage heat exchanger 130, which has a length of 2,100 mm (6.9 feet). This means that tube segment 135a is the lower end of tube 115a, tube segment 135b is the lower end of tube 115b, tube segment 135c is the lower end of tube 115c, and so on. As a result, the actual length of these coaxially continuous tubes is 6,700 mm (22 feet), equivalent to the distance between separable connection 105 and welded connection 145. The exit end of each tube segment 135a, 135b, 135c, can be attached, for example by welding or rolling, to the ISHX tubesheet (not shown per se, but located at the same position in the figure as welded connection 145). This design feature, in which the tubes of the first reaction stage are continuous with the tubes of the interstage heat exchanger, and wherein both the first reaction stage and the interstage heat exchanger share a common vessel shell, is referred to herein as an integrated interstage heat exchanger. It should be noted that interstage baffle 126 differs from a true tubesheet in that there are no tube-to-baffle attachments (e.g. welds); instead, the perforations through the interstage baffle 126 are of a slightly larger internal diameter than the outside diameter of the tubes (115 a, b, c), such that a small annular gap (not shown) of between 0.25 and 2.5 mm wide is formed around each tube. Because of this annular gap, a small volume of ISHX cooling salt (which is preferably supplied at a slightly higher pressure than the R1 cooling salt) may continuously pass through the interstage baffle and comingle with the R1 cooling salt circulation. Given the benefit of the present disclosure, means for recycling an appropriate volume of salt from the R1 circulation system back to the ISHX circulation system are easily specified by one of ordinary skill in the art of process engineering and need not be described in further detail herein.

In this embodiment, the R1 inlet tubesheet is 5,517 mm (18.1 feet) in diameter and comprises 22,000 tubes. FIG. 1c represents the layout of the R1 inlet tubesheet as viewed from above. This view shows that there is a circular region (indicated by the dashed circle) in the center of the tubesheet in which there are no tubes; this empty circular region has a diameter of about 1,144 mm (3.75 ft). The tubes have an internal diameter of 22.3 mm (0.878") and an external diameter 26.9 mm (1.060"). The tubes are arranged on a 60-degree triangular pattern, with a 34 mm (1.34") tubesheet pitch, resulting in a distance between the tubes of 7 mm (0.275"). From these dimensions, one can calculate the ratio of tube spacing (t) to the external diameter of the tube ($d_a$), as defined in U.S. Pat. No. 7,226,567:

$t=(26.9+7)$ and $d_a=(26.9)$, therefore $t/d_a=1.26$

Many R1 catalysts are commercially available and suitable for use in the SSOI reaction apparatus of the present invention. Examples include but are not limited to the first stage (R1) catalysts ACF, ACF-2, ACF-4, ACF-7, and ACF-8, all commercially available from Nippon Shokubai of Japan, and YX-38, YX-11 and YX-129, all commercially available from Nippon Kayaku of Japan. Some of these R1 catalysts are available in more than one size, for example ACF-7 catalyst is available as cylinders of both large and small dimensions, designated herein as ACF-7L (large) and ACF-7S (small), and may be used individually or in combination. Portions of the R1 tubes may also contain inert materials, such as for example 6.4 mm (0.25 inch) Denstone 57 spheres (available from Norton Chemical Process Products Corp, Akron Ohio, USA), to create preheating or cool-down zones at specified locations within each tube. Selection and installation of appropriate R1 catalysts and inerts in the tubes of the first reaction stage are within the ability of one of ordinary skill in the art.

High void fraction, turbulence inducing inserts can be placed within the tube segments (135 a, b, c) of the interstage heat exchanger to enhance heat transfer without the accumulation foulants. By high void fraction is meant greater than 85% void fraction and preferably greater than 90% void fraction. In this specific embodiment, a helical metal strip, herein referred to as a "twistee" insert, is placed within each tube. Each twistee insert is fabricated from a single rectangular strip of 1.57 mm (0.062 in) thick carbon steel, measuring 19.1 mm (0.750 in) wide by 2,057 mm (81 in) long. The strip can be mechanically twisted about its long axis to obtain a uniform helical geometry comprising one 360-degree revolution per foot (305 mm) of length and a final length of 2,032 mm (80 in). A metal ring of outside diameter 17.5 mm ($^{11}/_{16}$ in) can then formed from 1.6 mm ($^{1}/_{16}$ in) diameter wire and attached to the upstream end of the twistee, oriented perpendicular to the long axis of the twistee insert, in order to facilitate placement of the turbulence inducing insert inside the tube.

In some embodiments, a piece of 8×8 wire mesh, comprising 0.035 in (0.9 mm) wire, can also be affixed to the metal ring on the end of the twistee insert to form a planar, flow-through barrier, thereby allowing the upstream end of the twistee insert to function as a catalyst retaining device. The resulting twistee inserts can have a void fraction of about 92% and an effective external diameter that is about 85% of the internal diameter of the reactor tubes of this embodiment, allowing them to be easily installed and removed by hand. Given the benefit of the present disclosure, it will be evident that twistee inserts may also be fabricated for use in tubes of a different internal diameter. In at least one embodiment, the width of the initial metal strip (and the outside diameter of the attached upstream ring) ranges from between about 80 and 99.5% of the tube internal diameter.

Figure 1D:
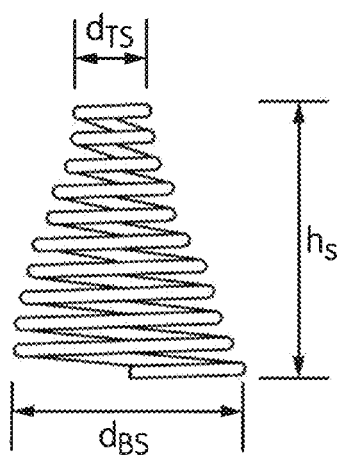
FIG. 1d is a side view of a conical catalyst retaining spring.

In other embodiments, modified twistee inserts can be used rather than affixing 8×8 wire mesh to the twistees. Such modified twistee inserts may comprise a conical catalyst retaining spring (see FIG. 1d) welded to the upstream end of one of the previously described twistee inserts. When used in a 22.3 mm (0.878 in) internal diameter ISHX tube, the conical spring can have, for example, a top external diameter, $d_{TS}$, of 6.1 mm (0.241 in) and a bottom external diameter, $d_{BS}$ of 19.1 mm (0.75 in)—equal to the effective diameter of the twistee insert. The conical catalyst retaining spring can be fabricated, for example, from eleven evenly-spaced coils of 1.47 mm (0.058 in) diameter stainless steel wire to form a conical spring with an overall height (h) of 25.4 mm (1 in) and coil spacing narrow enough to allow the upstream end of the modified twistee insert to function as a catalyst retaining device.

Figure 1E:
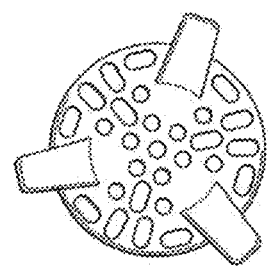
FIG. 1e is a top view of a catalyst retaining clip.

In at least one embodiment, twistee inserts can be installed in combination with a removable retaining device, such as, for example, a catalyst clip of the type illustrated in FIG. 1e, which are commercially available from MAN Turbo AG (formerly Deggendorfer Werft and Eisenbau GmbH) of Oberhausen, Germany, in order to retain them within the ends of the reactor tubes under process flow conditions.

Although the present embodiment utilizes twistee inserts within the interstage heat exchanger, various alternative turbulence inducing inserts have been disclosed in the literature and many of these are commercially available for use in heat exchanger tubes. Given the benefit of the present disclosure, it is within the ability of one of ordinary skill to select suitable high void fraction turbulence inducing inserts for use in the SSOI reactor design of the present invention; it should also be understood that, in at least one embodiment, the term "high void fraction turbulence inducing inserts" is not intended to encompass particulate-type inert materials, such as for example Denstone 57 inert spheres, which have a typical bulk void fraction of less than 50%. Examples of suitable, commercially available high void fraction turbulence inducing inserts include but are not limited to wire turbulators, disclosed in U.S. Pat. No. 4,201,736 and commercially available from Ormiston Wire Ltd of Isleworth, England; Kenics Static Mixer elements, commercially available from Chemineer, Inc. of Dayton, Ohio USA; and Twisted Tapes, commercially available from Koch Heat Transfer Company, LP of Houston, Tex. USA.

In at least one embodiment, the open interstage region 150 has, for example, a diameter of 5,517 mm (18.1 ft) and a length of 2,100 mm (6.9 ft). In accordance with at least one embodiment of the SSOI reactor design of the present invention, the open interstage region is at least partially filled with one or more stable, high surface area inert materials 151, in a quantity sufficient to provide at least 930 m$^2$ (10,000 sq ft) of total surface area for removal of foulants, such as, for example, at least 2,790 m$^2$ (30,000 sq ft), or 3,720 m$^2$ (40,000 sq ft).

In at least one embodiment, the inert materials may comprise at least one type of material selected from the group consisting of ceramic, mineral, metal and polymer.

In at least one embodiment relating to processes in which propylene is oxidized to acrylic acid, stable materials may be chosen from materials tolerant of temperatures of up to about 365° C., pressures of up to about 3 atm, and chemical compounds such as for example propylene, acrylic acid, carbon monoxide, acetic acid, and acrolein. Examples of stable, inert materials suitable for use in the SSOI reactor of the present invention include but are not limited to carbon steel, 316 stainless steel, monel, alumina, silica, silicon carbide, and porcelain.

Examples of stable, high surface area inert materials include but are not limited to 6 mm×6 mm aluminum raschig rings, 5 mm diameter silicon carbide spheres, 20 pore-per-inch (ppi) open-cell ceramic foam, 16 mm (⅝ in) diameter stainless steel Pall rings, or 13 mm MacroTrap™ Media 1.5 (available from Norton Chemical Process Products Corp, Akron Ohio, USA). Of course, given the teachings of the present disclosure, it is within the ability of one of ordinary skill in the art of process engineering to select other suitable stable, high surface area inert materials, not specifically named herein, for use with the inventive SSOI reactor.

The shell of open interstage region 150 may comprise two 832 mm (32.75 in) diameter lower manways (not shown in FIG. 1a), on opposite sides of the reactor (180 degrees apart), placed such that the lower manway centerline is located at a distance of about 500 mm (19.7 in) from the R2 inlet tubesheet 155. Additionally, the shell of open interstage region 150 may comprise two 667 mm (26.26 in) diameter upper manways (not shown in FIG. 1a), on opposite sides of the reactor (180 degrees apart), placed such that the manway centerline is located at a distance of about 420 mm (16.5 in) from the ISHX tubesheet 145. These manways can provide personnel access to the interior of open interstage region 150 for catalyst replacements and other maintenance work. The upper manways may also be beneficially employed for transferring particulate materials—such as loose-fill spheres, cylinders, tablets, pellets, and granules—into the open interstage region. In this embodiment, bulk 38 mm (1.5 in) diameter EnviroStone 66 ceramic spheres (available from Crystaphase Technologies, Inc of Houston Tex. USA) are placed into supply hoppers, connected by means of temporary conduits to the upper manways, and then transferred into the open interstage region by 'pouring' under the influence of gravity.

When the transfer is complete, the spheres, which self-assemble upon pouring into a bed with a void fraction of about 40% and surface-area-to-bulk-volume of 94.5 m$^2$ per cubic meter (28.8 sq ft per cubic foot), occupy about 93% of the volume within the open interstage region, leaving an empty space of about 150 mm (6 in) between the top of the EnviroStone 66 layer and the bottom surface of the ISHX tubesheet. The resulting bed of ceramic spheres has an average depth of 1,957 mm (6.4 ft) and occupies a bulk volume of 46.7 m$^3$ (1,650 ft$^3$), thereby providing more than 4,400 m$^2$ (47,300 ft$^2$) of surface area for removal of foulants.

In the foregoing embodiment, the second reaction stage 160 has a length of 4,500 mm (14.76 ft) and contains a plurality of seamless carbon steel tubes, represented generally in the figure as 165a, 165b, 165c. The entrance end of each tube in the second reaction stage can be attached, for example by welding or rolling, to the R2 inlet tubesheet (not shown per se, but located at the same position in the figure as welded connection 155). The exit end of each tube section 165a, 165b, 165c, can be attached, for example by welding or rolling, to the R2 exit tubesheet (not shown per se, but located at the same position in the figure as separable connection 175).

The R2 inlet tubesheet of this embodiment is 5,517 mm (18.1 ft) in diameter and comprises 22,000 tubes. The layout of the R2 inlet tubesheet is the same as the R1 inlet tubesheet (see FIG. 1c), including the empty circular region in the center of the tubesheet in which there are no tubes; this empty circular region also has a diameter of 1,144 mm (3.75 ft). The tubes within the second reaction stage have an internal diameter of 22.3 mm (0.878 in) and an external diameter 26.9 mm (1.060 in). The tubes are arranged on a 60-degree triangular pattern, with a 34 mm (1.34 in) tubesheet pitch, resulting in a distance between the tubes of 7 mm (0.275 in).

Many R2 catalysts are commercially available and suitable for use in the SSOI reaction apparatus of the present invention. Suitable second stage (R2) catalysts include but are not limited to ACS, ACS-2, ACS-6, ACS-7, and ACS-8, commercially available from Nippon Shokubai of Japan and T-202, commercially available from Nippon Kayaku of Japan. Some of these catalysts are also available in more than one size, for example ACS-7 catalyst is available as spheres in both large and small diameters, designated herein as ACS-7L (large) and ACS-7S (small), and may be used individually or in combination. Portions of the R2 tubes may also contain inert materials, such as for example 5 mm (3/16 in) diameter Silica-alumina support spheres (designated as "SA-5218" and available from Norton Chemical Process Products Corp, Akron Ohio, USA), to create preheating or cool-down zones at specified locations within each tube. Selection and installation of appropriate R2 catalysts and inerts in the tubes of the second reaction stage are within the ability of one of ordinary skill in the art.

In this embodiment, the twistee inserts within the interstage heat exchanger as well as the second reaction stage (R2) catalyst are both retained in the reactor tubes using catalyst support grid panels comprising wire mesh. The use of catalyst support grid panels comprising wire mesh may provide significant manpower and time savings during catalyst installation and removal as compared to the use of traditional catalyst clips or other in-tube retaining means. In this specific embodiment, the catalyst support grid panels comprise segments of 2.7 mm wire mesh formed from 0.6 mm diameter wire. The wire mesh segments are welded to a 15 mm thick (0.6 in) support plate, comprising a plurality of 22.3 mm diameter holes in a pattern that matches the specific geometry of the R2 outlet tubesheet; this results in a set of generally rectangular catalyst support grid panels, with a nominal rectangular dimensioning of about 918 mm×471 mm (36 in×18.5 in); panels to be fit along the circumference of the reactor tubesheet must of course deviate from a true rectangular shape due to the presence of one or more arcs, and therefore delineate a somewhat smaller area than the full-size rectangular panels.

In this embodiment, a total of 60 catalyst support grid panels are employed to retain the R2 catalyst within the tubes of the second reaction stage. Prior to the introduction of catalyst into the reactor tubes, each catalyst support grid panel can be placed with the wire mesh in direct contact with the bottom surface of the R2 outlet tubesheet and the panel can be secured with bolts that pass through solid regions of the panel and are anchored directly in the tubesheet. In at least one embodiment, the bolts can be permanently attached to the R2 outlet tubesheet and have sufficient exposed perpendicular length to extend completely through the catalyst support grid panel; the catalyst support grid panel can then secured in place using removable metal fasteners comprising two tines, such as cotter pins. The end of each bolt comprises a hole running perpendicular to the bolt's axis, through which the tines of the cotter pin passes; the two tines are then bent outward upon installation to secure the cotter pin to the bolt. Twistee inserts are also retained within the tubes of the interstage heat exchanger using similar catalyst support grid panels secured to the bottom surface of the ISHX tubesheet with bolts and cotter pins.

Although described herein in relation to the 22,000 tube SSOI reactor of this embodiment, the use of catalyst support grid panels comprising wire mesh will provide even greater benefits for large-scale commercial SSOI reactors, such as for example SSOI reactors comprising 25,000 tubes, 30,000 tubes, 45,000 tubes, or more. In the present invention, it is therefore most preferred that catalyst is retained within the tubes of SSOI reactors comprising 25,000 tubes or more with catalyst support grid panels comprising wire mesh. It will also be evident, given the present disclosure, that the catalyst support grid panels comprising wire mesh disclosed herein may be beneficially incorporated into other reactor designs, such as for example tandem reactors and SRS reactors. The present invention therefore further includes retaining catalyst within the tubes of tandem reactors or SRS reactors with catalyst support grid panels comprising wire mesh.

Referring now to FIG. 1b, this embodiment of the inventive SSOI reactor comprises three independently controlled coolant circulation systems, which provide the capability to individually adjust the temperature of each cooled section (110, 130, 160) as needed. HITEC® heat transfer salt, available from Coastal Chemical Co. of Houston, Tex. USA, is used as the coolant medium for all three circulation systems in this embodiment. The systems are herein referred to as the R1 salt circulation system, supporting the first reaction stage 110; the ISHX salt circulation system, supporting the interstage heat exchanger 130; and the R2 salt circulation system, supporting the second reaction stage 160.

Consistent with the at least one embodiment of the present invention, such a coolant system configuration may allow the process-side temperature of interstage heat exchanger to be controlled independently of the process temperature of the first reaction stage, allowing the process gas leaving the ISHX to be maintained at a temperature of at least 240° C. and not more than 280° C. Although not an essential feature of the inventive design, this embodiment also provides the capability of controlling the process-side temperature of the second reaction stage independently of the process temperature of the interstage heat exchanger; such additional capability to control the oxidation process operation is used in at least one embodiment of the present invention.

Each of the three coolant circulation systems in this embodiment may comprise one or more salt circulation pumps, waste heat boilers, and associated transfer piping (not shown), through which the exothermic heat of the oxidation reaction can be recovered to produce byproduct steam. Optional equipment, such as salt storage tanks, gas-fired salt heaters, integral thermal expansion vessels (also known as "salt bustles"), and salt transfer pumps may also be included in the salt circulation system. Furthermore, each of these circulation systems may comprise instrumentation (not shown), such as thermocouples, and automated controls, such as flow control valves, to maintain the temperature and circulation rate of the salt supplied to the reactor at desired target values.

For the R1 salt circulation system supporting section 110, cool salt may enter via the R1 supply lines 121 near the bottom of the section and can be uniformly distributed about the circumference of the reactor through an entrance channel (not shown), comprising internal flow distribution means such as one or more of baffles, flow vanes, weirs, screens, and perforated-plate distributors, and commonly referred to as a "lower salt manifold". Once inside the reactor shell, the salt may flow upward, repeatedly traversing the reactor shell in the radial direction by flowing around a series of evenly-spaced shellside plates known in the art of heat exchange as "double segmental baffles" 122. This radial flow pattern may ensure good salt-to-tube contact in order to achieve high heat removal efficiency from the tubes. Upon reaching the top of the R1 section, the warm salt can be collected via another circumferential exit channel (not shown), which may optionally comprise flow distribution means, commonly referred to as an "upper salt manifold" and can be transferred via the R1 return lines 123 to waste heat boilers (not shown).

For the ISHX salt circulation system supporting section 130, cool salt may enter via the ISHX supply lines 141 near the bottom of the section and may be uniformly distributed about the circumference of the reactor through an entrance channel ("lower salt manifold", not shown), comprising internal flow distribution means such as one or more of baffles, flow vanes, weirs, screens, and perforated-plate distributors. Once inside the reactor shell, the salt can flow upward, repeatedly traversing the reactor shell in the radial direction by flowing around a series of evenly-spaced double segmental baffles 142. Upon reaching the top of the ISHX section, the warm salt can be collected via another circumferential exit channel ("upper salt manifold"—not shown), which may optionally comprise flow distribution means, and is transferred via the ISHX return lines 143 to waste heat boilers (not shown).

Similarly, for the R2 salt circulation system supporting section 160, cool salt may enter via the R2 supply lines 171 near the bottom of the section and can be uniformly distributed about the circumference of the reactor through a "lower salt manifold" (not shown), comprising internal flow distribution means such as one or more of baffles, flow vanes, weirs, screens, and perforated-plate distributors. Once inside the reactor shell, the salt may flow upward, repeatedly traversing the reactor shell in the radial direction by flowing around a series of evenly-spaced double segmental baffles 172. Upon reaching the top of the R2 section, the warm salt can be collected via another circumferential "upper salt manifold" (not shown), which may optionally comprise flow distribution means, and is transferred via the R2 return lines 173 to waste heat boilers (not shown).

The configuration of coolant flows moving in a direction generally opposite to the process flow (in this case, salt flowing upward through the shell while the process gas flows downward through the tubes) is commonly referred to as a counter-current coolant circulation. It should be noted that an alternative configuration wherein the coolant flows generally downward through the shell and the process gas flows upward through the tubes would also be considered a counter-current coolant circulation. Further, although the present embodiment comprises three coolant circulation systems of the same configuration, it should be recognized that in some cases it may be beneficial to configure some coolant circulations as counter-current while other circulations within the same reactor may be configured as co-current; such heterogeneous configurations are known as "hybrid" coolant circulations.

Figure 2:
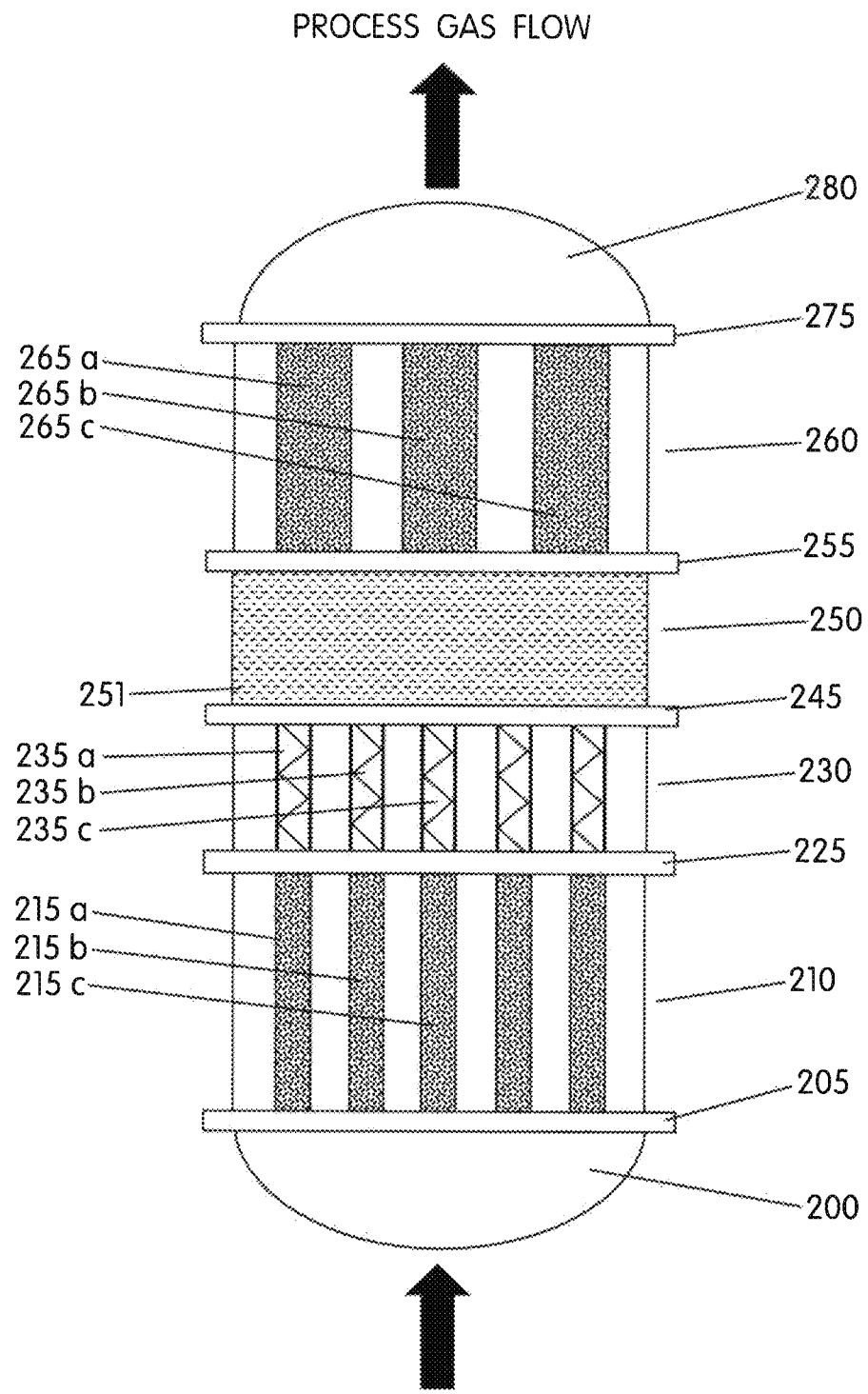
FIG. 2 is a side view representing the tubeside (process) features for a second embodiment of an SSOI reactor.

A process "upflow" configuration of the inventive SSOI reactor is illustrated in FIG. 2. Feed gases (comprising propylene, steam, oxygen, and nitrogen) enter the reactor from the bottom, flow vertically upward through the reactor, and exit the reactor at the top.

Major sections of the reactor include the inlet head 200, the first reaction stage 210 (also referred to herein as "R1"), the interstage heat exchanger 230 (also referred to herein as "ISHX"), the open interstage region 250, the second reaction stage 260 (also referred to herein as "R2"), and the outlet head 280. Interfaces 225, 245, and 255 are all permanent (e.g., welded) connections, while interfaces 205 and 275 are separable connections, allowing reactor heads 200 and 280 to be removed for maintenance.

The first reaction stage 210 contains a plurality of tubes, represented generally in the figure as 215a, 215b, 215c. The entrance end of each of these tubes is attached, for example by welding or rolling, to the R1 inlet tubesheet (not shown per se, but located at the same position as separable connection 205). The interstage heat exchanger 230 also contains a plurality of tubes, generally represented in the figure as 235a, 235b, 235c, and equivalent in number, diameter, and placement to the tubes of the first reaction stage. The exit end of each ISHX tube segment 235a, 235b, 235c, can be attached, for example by welding or rolling, to the ISHX tubesheet (not shown per se, but located at the same position in the figure as welded connection 245).

The tubes of the interstage heat exchanger are said to be coaxially continuous with the R1 tubes of the first reaction stage, meaning that tube segment 235a is the upper end of tube 215a, tube segment 235b is the upper end of tube 215b, tube segment 235c is the upper end of tube 215c, and so on. As previously noted, the direct connection of the interstage heat exchanger to the first reaction stage is referred to herein as an integrated interstage heat exchanger.

The R1 shellside coolant circulation can be separated from the ISHX shellside coolant by an interstage baffle (not shown per se, but located at the same position in the figure as connection 225); each of the coaxially continuous tubes extending from the R1 inlet tubesheet to the ISHX exit tubesheet can pass through this interstage baffle. It should be noted that the interstage baffle differs from a true tubesheet in that there are no tube-to-baffle attachments; instead, the perforations through the interstage baffle are of a slightly larger internal diameter than the outside diameter of the tubes (215 a, b, c), such that a small annular gap (not shown) of between 0.25 and 2.5 mm wide is formed around each tube. The R1 shellside coolant circulation (not shown) may be arranged in a co-current or in a counter-current configuration; similarly, the ISHX shellside coolant circulation may be arranged in a co-current or in a counter-current configuration as well, and need not match the configuration of the R1 shellside coolant circulation.

In at least one embodiment, the open interstage region 250 contains no tubes. In accordance with the SSOI reactor design of at least one embodiment of the present invention, the open interstage region can be at least partially filled with one or more stable, high surface area inert materials 251, in a quantity sufficient to provide at least 930 m$^2$ (10,000 sq ft) of total surface area for removal of foulants, preferably at least 2,790 m$^2$ (30,000 sq ft), and most preferably 3,720 m$^2$ (40,000 sq ft).

The second reaction stage 260 may contain a plurality of tubes, represented generally in the figure as 265a, 265b, 265c. The entrance end of each tube in the second reaction stage may be attached, for example by welding or rolling, to the R2 inlet tubesheet (not shown per se, but located at the same position in the figure as welded connection 255). The exit end of each tube section 265a, 265b, 265c, may be attached, for example by welding or rolling, to the R2 exit tubesheet (not shown per se, but located at the same position in the figure as interface 275). A novel feature of the embodiment illustrated in FIG. 2 is that one or more of the number, diameter, and placement of the tubes of the second reaction stage (the R2 tubes) is different than the tubes in the first reaction stage (the R1 tubes).

One embodiment of the reactor of FIG. 2 has a nominal annual production capacity of 120 kT of acrylic acid. The coolant medium used in this embodiment is Dowtherm™ heat transfer fluid, available from Dow Chemical Co. of Midland, Mich. USA. In this embodiment, there are 22,669 first reaction stage (R1) tubes and 14,523 second reaction stage (R2) tubes. The R1 tubes are 25.4 mm (1 in) in internal diameter and 4,700 mm (15.4 ft) long (from R1 tubesheet to interstage baffle) and the R2 tubes are 31.8 mm (1.25 in) in internal diameter and 4,500 mm (14.75 feet) long. The previously-described twistee inserts are installed in each ISHX tube segment. The open interstage region of this embodiment has a total volume of 40 m$^3$ (1,413 ft$^3$) and is completely filled with 16 mm (⅝ in) stainless steel Pall rings as the inert material. Such Pall rings have a void fraction of 93% and a specific surface area of 316 m²/m³, thereby providing a total surface area within the open interstage region of over 41,480 m² (446,500 sq ft). The Interstage Residence Time for this embodiment is 3 seconds.

An alternative embodiment of the reactor of FIG. 2 also has a nominal annual production capacity of 120 kT of acrylic acid. In this embodiment, however, there are 29,410 first reaction stage (R1) tubes and 22,672 second reaction stage (R2) tubes. The R1 tubes are 22.3 mm (0.878 in) in internal diameter and 4,600 mm (15.1 ft) long (from R1 tubesheet to interstage baffle) and the R2 tubes are 25.4 mm (1 in) in internal diameter and 4,200 mm (13.8 ft) long. Rather than placing the previously-described twistee inserts inside the ISHX tubes, the ISHX tubes of this embodiment are instead constructed using "Twisted Tubes", which are a special helical tube design which induces turbulent flow without the use of turbulence inducing inserts; Twisted Tubes are commercially available from Koch Heat Transfer Company, LP of Houston, Tex. USA. The open interstage region has a total length of 2,438 mm (8 ft) and is filled with 2 in diameter EnviroStone 66 spheres, providing a total surface area of over 4,450 m² (48,000 sq ft) and an Interstage Residence Time of about 2.1 seconds. The coolant medium used in this embodiment is HITEC® heat transfer salt.

Figure 3A:
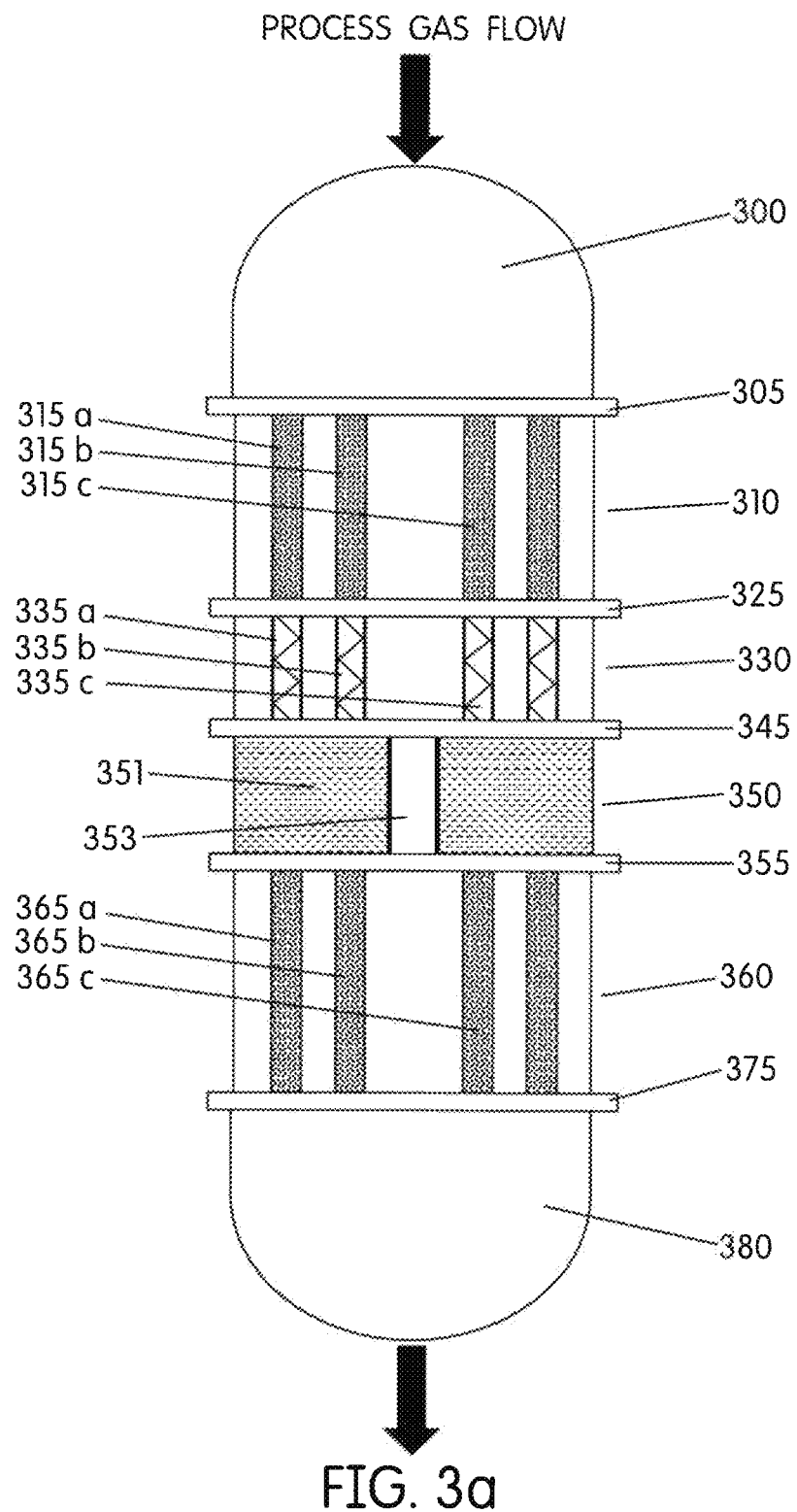
FIG. 3a is a side view representing the tubeside (process) features for a third embodiment of an SSOI reactor.
Figure 3B:
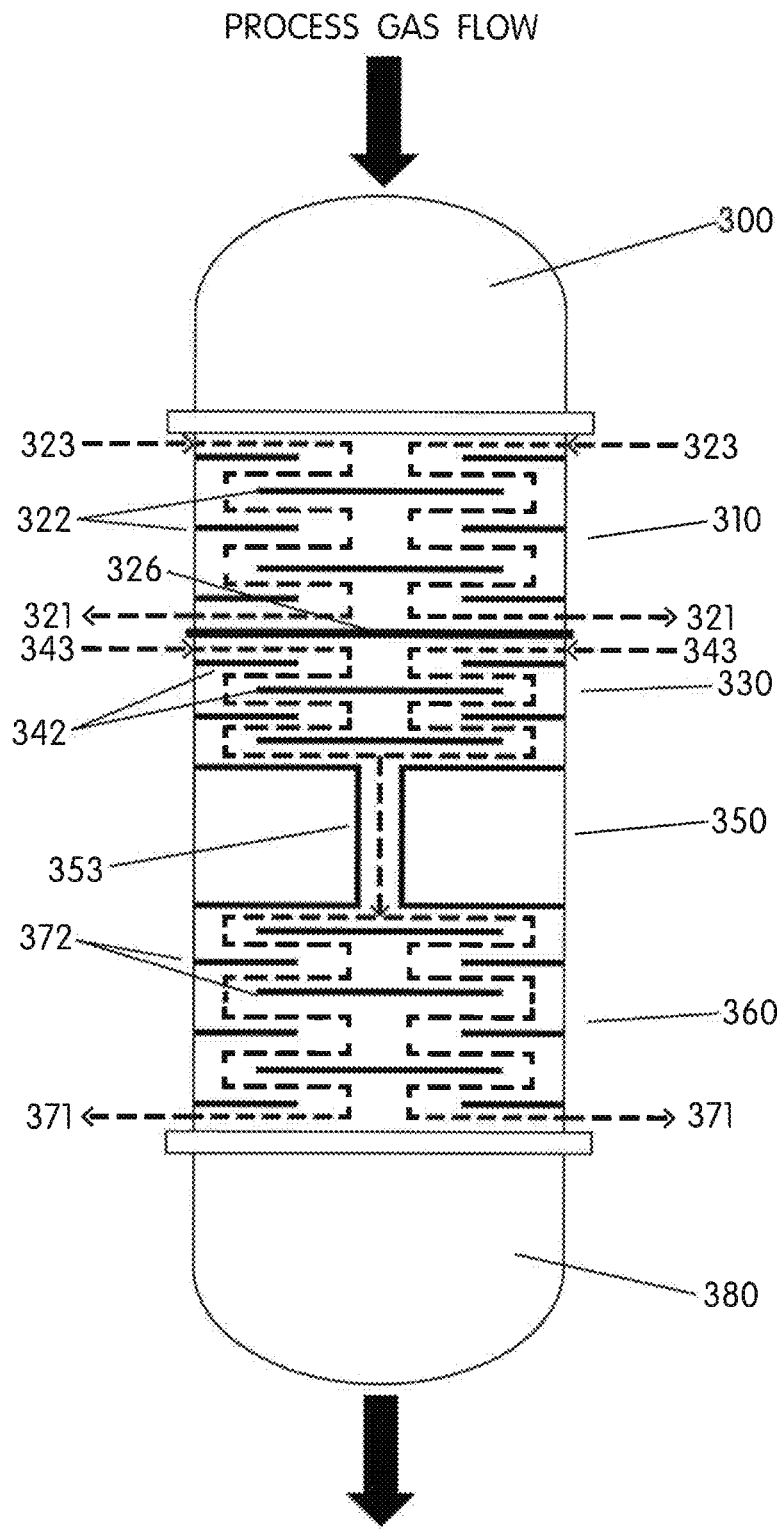
FIG. 3b is a side view representing the shellside (coolant) features for a third embodiment of an SSOI reactor.

FIGS. 3a and 3b in combination represent another embodiment of the inventive Single Shell Open Interstage (SSOI) reactor design comprising more than 16,000 tubes. The reactor of this embodiment has a shell diameter of about 4,800 mm (15.75 ft) and an overall length of more than 18,290 mm (60 ft). At typical feed ratios and a design propylene feed rate of 2,935 Nm³/hr (110 MSCFH), the reactor of this embodiment has a nominal annual production capacity of about 63 kT of acrylic acid.

Feed gases (which may comprise, for example, propylene, steam, oxygen, and nitrogen) enter the reactor from the top (see FIG. 3a), flow vertically downward through the reactor, and exit the reactor at the bottom, i.e., downflow operation.

Major sections of the reactor include the inlet head 300, the first reaction stage 310 (also referred to herein as "R1"), the interstage heat exchanger 330 (also referred to herein as "ISHX"), the open interstage region 350, the second reaction stage 360 (also referred to herein as "R2"), and the outlet head 380. Unless otherwise specified, all reactor components in this embodiment are constructed of carbon steel. The interfaces between adjacent sections, identified in the figures as 305, 325, 345, 355 and 375 can all be permanent (e.g., welded) connections.

Reactor inlet head 300 is about 4,040 mm (13.25 feet) in height and is not removable. It comprises a plurality of 610 mm (24 in) manways (not shown) on the sides and top of the head for maintenance access. The inlet head further comprises a 508 mm (20 in) process gas inlet nozzle.

In accordance with this embodiment, the first reaction stage 310 has a length of 4,600 mm (15.1 ft) and contains a plurality of seamless carbon steel tubes, represented generally in the figure as 315a, 315b, 315c. The entrance end of each tube in the first reaction stage is attached, for example by welding or rolling, to the R1 inlet tubesheet (not shown per se, but located at the same position in the figure as connection 305). Each tube within the first reaction stage 310 extends through interstage baffle 326 (refer to FIG. 3b) and passes completely through the interstage heat exchanger 330, which has a length of 1,956 mm (6.4 feet). This means that tube section 335a is the lower end of tube 315a, tube section 335b is the lower end of tube 315b, tube section 335c is the lower end of tube 315c, and so on. As a result, the actual length of these coaxially continuous tubes is about 6,556 mm (21.5 feet), equivalent to the distance between interfacial connection 305 and interfacial connection 345. The exit end of each tube segment 335a, 335b, 335c, is attached, for example by welding or rolling, to the ISHX tubesheet (not shown per se, but located at the same position in the figure as welded connection 345). As previously described, this design feature is referred to herein as an integrated interstage heat exchanger. It should be noted that in this embodiment, the interstage baffle 326 differs from a true tubesheet in that there are no tube-to-baffle welds; instead, the perforations through the interstage baffle 326 are of a slightly larger internal diameter than the outside diameter of the tubes (315 a, b, c), such that a small annular gap (not shown) of between 0.25 and 2.5 mm wide is formed around each tube. Because of this annular gap, a small volume of ISHX cooling salt (which is preferably supplied at a slightly higher pressure than the R1 cooling salt) may continuously pass through the interstage baffle and comingle with the R1 cooling salt circulation. Given the benefit of the present disclosure, means for recycling an appropriate volume of salt from the R1 circulation system back to the ISHX circulation system are easily specified by one of ordinary skill in the art of process engineering and need not be described in further detail herein.

As indicated generally in FIG. 3a, the first reaction stage region of the reactor may comprise an empty cylindrical volume located at the center of the tubesheet, and aligned with the longitudinal axis of the reactor, in which there are no tubes; this empty cylindrical volume has an average diameter of more than 610 mm (2 ft) and extends through the ISHX as well. The remaining annular volume in the first reaction stage and the ISHX comprises more than 16,000 coaxially continuous tubes. Each of these continuous tubes has an internal diameter of 22.3 mm (0.878 in) and an external diameter 27.3 mm (1.074 in). The tubes are arranged on a 60-degree triangular pattern, with a 33.73 mm (1.328 in) tubesheet pitch, resulting in a distance between the tubes of about 6.5 mm (0.254 in).

To retain catalyst within these continuous tubes, a plurality of the previously-described catalyst support grid panels comprising wire mesh can be directly attached to the ISHX outlet tubesheet 345. Each of the continuous tubes may then be loaded as follows, beginning with the upstream (entrance) end of the tube:

282 mm (11 in) of 3/16 inch diameter (4.75 mm) SA-5218 silica-alumina support spheres (available from Norton Chemical Process Products Corp, Akron Ohio, USA)

905 mm (36 in) of ACF7-L (large cylinder) catalyst 3,413 mm (134 in) of ACF7-S (small cylinder) catalyst 51 mm (2 in) of 5/16 in diameter silicon carbide rings (available from Norton Chemical Process Products Corp, Akron Ohio, USA)

a 1,905 mm (75 in) long Twistee turbulence inducing insert, fitted with optional 8×8 wire mesh on the upstream end This loading schedule results in a charge of 1.273 kg of total ACF7 catalyst (large+small size cylinders) in each first reaction stage tube.

In this embodiment, the residence time of process gas through the Interstage Heat Exchanger is found to be 0.96 seconds.

The open interstage region 350 of this embodiment has a total length of 2,134 mm (7 ft). Its shell comprises two 610 mm (24 in) diameter lower manways (not shown in FIG. 3a), on opposite sides of the reactor (180 degrees apart), placed such that the lower manway centerline is located at a distance of about 356 mm (14 in) from the R2 inlet tubesheet 355. Additionally, the shell of open interstage region 350 comprises two 610 mm (24 in) diameter upper manways (not shown), on opposite sides of the reactor (180 degrees apart), placed such that the manway centerline is located at a distance of about 356 mm (14 in) from the ISHX tubesheet 345. These manways can provide personnel access to the interior of open interstage region 350 for catalyst replacements and other maintenance work. The upper manways may also be beneficially employed for transferring particulate materials—such as loose-fill spheres, cylinders, tablets, pellets, and granules—into the open interstage region such as by pouring.

As indicated generally in FIG. 3a, the open interstage region comprises a 610 mm (2 ft) diameter internal salt transfer pipe 353, aligned with the longitudinal axis of the reactor. Internal salt transfer pipe 353 extends across the length of the open interstage region, from the ISHX tubesheet 345 to the R2 inlet tubesheet 355, and further comprises an integral expansion joint (not shown) to accommodate thermal growth. In this embodiment, about 75% of the remaining annular volume of the open interstage region is filled with bulk 38 mm (1.5 in) diameter Denstone 2000 inert spheres (available from Norton Chemical Process Products Corp, Akron Ohio, USA), indicated generally as 351 in FIG. 3a.

In at least one embodiment, the inert spheres, which self-assemble upon pouring into a bed with a void fraction of about 40% and surface-area-to-bulk-volume of 94.5 $m^2/m^3$ (28.8 $ft^2/ft^3$), form a bed with an average depth of about 1,600 mm (5.25 ft), and leave an empty space of about 533 mm (1.75 ft) between the top of the Denstone 2000 layer and the bottom surface of the ISHX tubesheet. Thus, the bed of ceramic spheres occupies a bulk volume of 28.5 $m^3$ (1,006 $ft^3$), and provides more than 2,690 $m^2$ (28,965 sq ft) of surface area for removal of foulants.

The residence time of the process gas through the open interstage region is found to be 1.79 seconds. Summing the residence times through the ISHX and the Open Interstage Region yields a combined interstage residence time of 2.75 seconds.

In this embodiment, the second reaction stage 360 has a length of 2,925 mm (9.6 ft) and contains a plurality of seamless carbon steel tubes, represented generally in the figure as 365a, 365b, 365c. The entrance end of each tube in the second reaction stage is attached, for example by welding or rolling, to the R2 inlet tubesheet (not shown per se, but located at the same position in the figure as welded connection 355). The exit end of each tube section 365a, 365b, 365c, is attached, for example by welding or rolling, to the R2 exit tubesheet (not shown per se, but located at the same position in the figure as welded connection 375).

As indicated generally in FIG. 3a, the second reaction stage region of the reactor may comprise an empty cylindrical volume located at the center of the tubesheet, and aligned with the longitudinal axis of the reactor, in which there are no tubes; this empty cylindrical volume has a diameter of more than 610 mm (2 ft). The remaining annular volume of the second reaction stage comprises more than 16,000 tubes, arranged in the same manner as the first reaction stage, and each of these tubes has an internal diameter of 22.3 mm (0.878 in) and an external diameter 27.3 mm (1.074 in). As with the first reaction stage, these tubes are arranged on a 60-degree triangular pattern, with a 33.73 mm (1.328 in) tubesheet pitch.

To retain catalyst within the tubes of the second reaction stage, a plurality of the previously-described catalyst support grid panels comprising wire mesh may be directly attached to the R2 outlet tubesheet 375. Each of the second reaction stage tubes can then loaded as follows, beginning with the upstream (entrance) end of the tube:
- 102 mm (4 in) of 3/16 in diameter (4.75 mm) SA-5218 silica-alumina support spheres (available from Norton Chemical Process Products Corp)
- 800 mm (31.5 in) of ACS7-L (large sphere) catalyst
- 2,023 mm (79.6 in) of ACF7-S (small sphere) catalyst This loading schedule results in a charge of 1.338 kg of total ACS7 catalyst (large+small size spheres) in each second reaction stage tube, and an overall Catalyst Mass Ratio of 1.05 for the reactor.

Reactor outlet head 380 is about 3,430 mm (11.25 ft) in height and is not removable. It comprises two 610 mm (24 in) manways (not shown) on the bottom of the head for maintenance access. The outlet head further comprises a 610 mm (24 in) process gas outlet nozzle.

Referring now to FIG. 3b, this embodiment of the inventive SSOI reactor comprises two independently controlled coolant circulation systems: the R1 salt circulation system, supporting the first reaction stage 310, and the ISHX/R2 salt circulation system, supporting the interstage heat exchanger 330 and the second reaction stage 360 combined. HITEC® heat transfer salt, available from Coastal Chemical Co. of Houston, Tex. USA, is used as the coolant for both of the circulation systems in this embodiment.

Consistent with the teachings of the present disclosure, such a coolant system configuration allows the process-side temperature of interstage heat exchanger to be controlled independently of the process temperature of the first reaction stage, enabling the process gas leaving the ISHX to be maintained, for example, at a temperature of at least 240° C. and not more than 280° C. It should be noted, however, that in this embodiment, the process-side temperature of the second reaction stage is not controlled independently of the process temperature of the interstage heat exchanger.

Each of these circulation systems may comprise one or more salt circulation pumps, waste heat boilers, and associated transfer piping (not shown), through which the exothermic heat of the oxidation reaction can be recovered to produce byproduct steam. Optional equipment, such as salt storage tanks, gas-fired salt heaters, integral thermal expansion vessels (also known as "salt bustles"), and salt transfer pumps may also be included in the salt circulation system. Furthermore, each of these circulation systems may comprise instrumentation (not shown), such as thermocouples, and automated controls, such as flow control valves, to maintain the temperature and circulation rate of the salt supplied to the reactor at desired target values.

For the R1 salt circulation system supporting section 310, cool salt enters via the R1 supply lines 323 near the top of the section and is uniformly distributed about the circumference of the reactor through an entrance channel (not shown), comprising internal flow distribution means such as one or more of baffles, flow vanes, weirs, screens, and perforated-plate distributors, and commonly referred to as an "upper salt manifold." Once inside the reactor shell, the salt flows downward, repeatedly traversing the reactor in the radial direction by flowing around a series of eleven shell-side plates, placed at intervals of about 380 mm (1.25 ft) apart, and known in the art of heat exchange as "double segmental baffles" (shown generally as 322). This radial flow pattern ensures good salt-to-tube contact in order to achieve high heat removal efficiency from the tubes. Upon reaching the bottom of the R1 section, the warm salt can be collected via another circumferential exit channel (not shown), which may optionally comprise flow distribution means, commonly referred to as a "lower salt manifold" and can be transferred via the R1 return lines 321 to waste heat boilers (not shown).

For the ISHX/R2 salt circulation system supporting sections 330 and 360, cool salt enters via the ISHX supply lines 343 near the top of section 330 and is uniformly distributed about the circumference of the reactor through an entrance channel, comprising internal flow distribution means such as one or more of baffles, flow vanes, weirs, screens, and perforated-plate distributors ("upper salt manifold", not shown). Once inside the reactor shell, the salt flows downward, repeatedly traversing the reactor in the radial direction by flowing around a series of four double segmental baffles 342, placed at intervals of about 366 mm (1.20 ft) apart. Upon reaching the bottom of the ISHX section, the salt can be transferred across the open interstage region 350 by flowing downward through internal salt transfer pipe 353 and into R2 section 360. Once inside the shell of the R2 section 360, the salt may continue to traverse the reactor shell in the radial direction by flowing downward around another series of six Double Segmental Baffles (372), placed at intervals of about 390 mm (1.30 feet) apart. Upon reaching the bottom of the R2 section, the warm salt can be collected via another circumferential exit channel, which may optionally comprise flow distribution means, ("lower salt manifold"—not shown) and transferred via the R2 return lines 371 to waste heat boilers (not shown).

This configuration of salt flows moving in a direction generally equivalent to the process flow (in this case, salt flowing downward through the shell while the process gas flows downward through the tubes) is commonly referred to as a co-current coolant circulation. It should be noted that an alternative configuration wherein the salt flows generally upward through the shell and the process gas flows upward through the tubes would also be considered a co-current coolant circulation.

Figure 4:
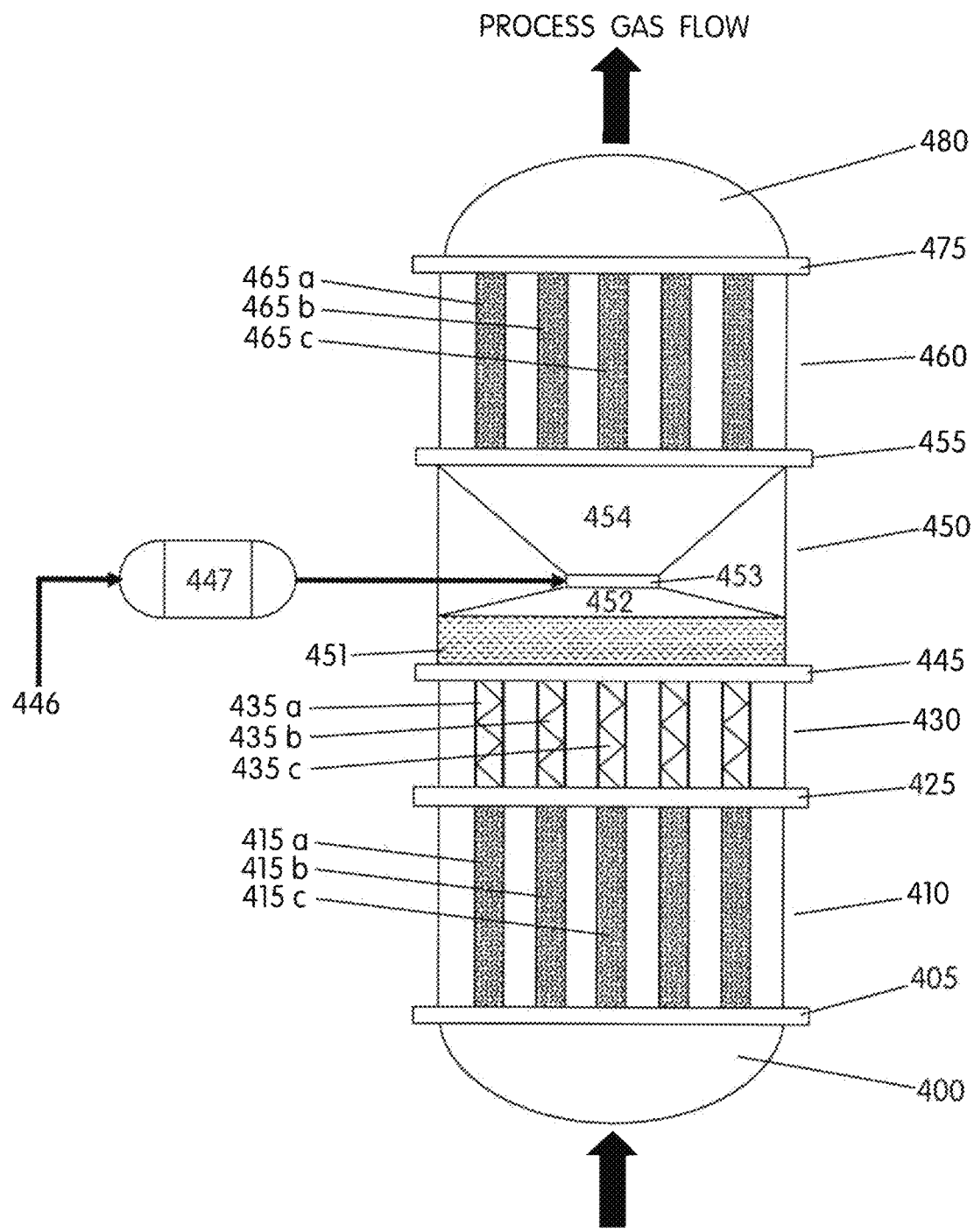
FIG. 4 is a side view representing the tubeside (process) features for one embodiment of an SSOI reactor comprising mixing means for supplemental oxidant addition.

FIG. 4 represents another embodiment of the inventive Single Shell Open Interstage (SSOI) reactor design comprising 22,000 tubes, each with an internal diameter of 22.3 mm (0.878 in). The reactor of this embodiment has a shell diameter of about 5,600 mm (18.4 ft) and an overall length of more than 15,240 mm (50 ft). This reactor embodiment further comprises means for supplemental oxidant addition to the interstage region of the reactor. The operating flexibility provided by supplemental oxidant addition allows some of the oxygen normally fed to the first reaction stage to be relocated to a point downstream of R1, resulting in an increased propylene:air mole ratio in the reactor feed, and a favorable reduction in flammability of the reactor feed gas. As will be described in more detail below, supplemental oxidant addition may also allow the reactor to efficiently operate at higher propylene design feed rates, relative to similarly-sized SSOI reactors, thereby providing increased acrylic acid production capacity. For example, at typical feed ratios the reactor of this embodiment has a nominal annual production capacity of about 110 kT of acrylic acid as compared to the reactor embodiment of FIG. 1a, which also comprises 22,000 tubes of 22.3 mm internal diameter, but has a nominal annual production capacity of only about 100 kT of acrylic acid.

Referring to FIG. 4, feed gases (e.g., propylene, steam, oxygen, and nitrogen) enter the reactor from the bottom, flow vertically upward through the reactor, and exit the reactor at the top. This arrangement is therefore known as an "upflow" process configuration.

Major sections of the reactor include the inlet head 400, the first reaction stage 410 (also referred to herein as "R1"), the interstage heat exchanger 430 (also referred to herein as "ISHX"), the open interstage region 450, the second reaction stage 460 (also referred to herein as "R2"), and the outlet head 480.

The interfacial connections between adjacent sections, identified in the figures as 405, 425, 445, 455, and 475, may comprise permanent (e.g., welded) connections or may optionally comprise separable connections, such as flanged connections secured with a plurality of fasteners, such as for example bolts or clamps. In the embodiment of FIG. 4, interfaces 405 and 475 are separable connections, allowing inlet head 400 and outlet head 480 to be easily removed for catalyst replacement; further, interfaces 445 and 455 may also be separable connections, thereby providing improved maintenance access to components within the open interstage region 450. Interface 425 can be a welded connection.

The first reaction stage 410 has a length of 4,600 mm (15 ft) and contains a plurality of tubes, represented generally in the figure as 415a, 415b, 415c. The entrance end of each of these tubes is attached, for example by welding or rolling, to the R1 inlet tubesheet (not shown per se, but located at the same position as separable connection 405). The R1 inlet tubesheet is 5,517 mm (18.1 ft) in diameter and comprises 22,000 tubes. The tubes have an internal diameter of 22.3 mm (0.878 in) and an external diameter 26.9 mm (1.060 in). The tubes are arranged on a 60-degree triangular pattern, with a 34 mm (1.34 in) tubesheet pitch, resulting in a distance between the tubes of 7 mm (0.275 in).

The interstage heat exchanger 430 may also contain a plurality of tubes, generally represented in the figure as 435a, 435b, 435c, and equivalent in number, diameter, and placement to the tubes of the first reaction stage. The exit end of each ISHX tube segment 435a, 435b, 435c, may be attached, for example by welding or rolling, to the ISHX tubesheet (not shown per se, but located at the same position in the figure as interfacial connection 445).

The tubes of the interstage heat exchanger can be coaxially continuous with the R1 tubes of the first reaction stage, meaning that tube segment 435a is the downstream end of tube 415a, tube segment 435b is the downstream end of tube 415b, tube segment 435c is the downstream end of tube 415c, and so on. As previously noted, such direct connection of the interstage heat exchanger to the shell and tubes of the first reaction stage is referred to herein as an integrated interstage heat exchanger.

High void fraction, turbulence inducing inserts are placed within the tube segments (435 a, b, c) of the interstage heat exchanger to enhance heat transfer without the accumulation foulants. In this specific embodiment, a twistee insert is placed within each ISHX tube segment.

The R1 shellside coolant circulation is separated from the ISHX shellside coolant by an interstage baffle (not shown per se, but located at the same position in the figure as connection 425); each of the coaxially continuous tubes extending from the R1 inlet tubesheet to the ISHX exit tubesheet may pass through this interstage baffle. As previously described, the interstage baffle differs from a true tubesheet in that there may be no tube-to-baffle welds; instead, the perforations through the interstage baffle are of a slightly larger internal diameter than the outside diameter of the tubes (415 a, b, c), such that a small annular gap (not shown) of between 0.25 and 2.5 mm wide is formed around each tube. The R1 shellside coolant circulation may be arranged in a co-current or in a counter-current configuration; similarly, the ISHX shellside coolant circulation may be arranged in a co-current or in a counter-current configuration as well, and need not match the configuration of the R1 shellside coolant circulation.

The open interstage region 450 contains no tubes and has a total length of 3,137 mm (10.3 ft). In accordance with the SSOI reactor design of the present invention, the open interstage region is at least partially filled with one or more stable, high surface area inert materials 451, in a quantity sufficient to provide at least 930 m$^2$ (10,000 sq ft) of total surface area for removal of foulants, such as, for example, at least 2,790 m$^2$ (30,000 sq ft), or at least 3,720 m$^2$ (40,000 square feet). In this embodiment, the stable, high surface area inert material is 20 ppi ("pores-per-inch") ceramic foam tiles, of generally rectangular shape and available in thicknesses of between about 12 mm and 305 mm (between 0.5 and 12 inches). Suitable ceramic foam tiles are commercially available from several suppliers, including: Ultramet of Pacoima, Calif. USA; ERG Aerospace Corporation of Oakland, Calif. USA; Selee Corporation of Hendersonville, N.C. USA; and Sud-Chemie Hi-Tech Ceramics of Alfred, N.Y. USA.

The specific 20 ppi ceramic foam tiles of this embodiment have a thickness of 51 mm (2 inches), a relative density of 8%, a void fraction of 92%, and an effective surface area of about 1,260 m$^2$/m$^3$ (384 ft$^2$/ft$^3$). These ceramic foam tiles can be placed directly upon the ISHX exit tubesheet 445 and fitted together to uniformly cover the entire surface of the tubesheet. Multiple layers of tiles are stacked to attain a continuous ceramic foam bed with a planar top surface and a uniform thickness of 152.4 mm (6 in). Such a ceramic foam bed provides a total surface area of more than 4,550 m$^2$ (49,000 sq ft) for removal of foulants.

Within the open interstage region 450 and immediately downstream of the ceramic foam bed is a supplemental oxidant mixing assembly. In this embodiment, the specific mixing assembly is herein referred to as a "venturi-mixer", but other supplemental oxidant mixing assemblies may also be utilized without deviating from the spirit of the present invention.

Supplemental oxidant supply line 446 provides supplemental oxidant, comprising, for example, oxygen and optionally one or more inerts, such as for example nitrogen, water, or carbon dioxide, as a gas stream to the venturi-mixer.

Optional oxidant heat exchanger 447 may be used to adjust the temperature of the supplemental oxidant before it reaches the venturi-mixer. Optional flow control means, such as for example a flow control valve (not shown) may also be present in supplemental oxidant supply line 446.

The venturi-mixer of this embodiment comprises three sections, interconnected to form a continuous, flow-through mixing assembly: an inlet contracting section 452, an intermediate throat section 453, and an outlet expanding section 454. The overall length of the venturi-mixer is 2,985 mm (9.79 ft).

In this embodiment, the inlet contracting section 452 is a truncated cone with an inlet diameter of 5,517 mm (18.1 ft), an outlet diameter of 1,219 mm (4 ft), an overall length of 378 mm (1.24 ft) and an included angle of 160 degrees. Optionally, contracting section 452 comprises a plurality of separable segments, or "staves", each with a geometry selected to allow easy passage of the staves through an access manway (not shown) on the shell wall of open interstage region 450. The use of such separable segments may improve maintenance access within the open interstage region and may reduce the need to use separable connections at interfaces 445 and 455.

The intermediate throat section 453 is a cylinder with an internal diameter of 1,219 mm (4 ft) and an overall length of 457 mm (18 in); this throat section comprises one or more blending elements (not shown) selected from the list including nozzles, injectors, gas-gas mixing elements, distributors, aspirators, coanda-effect mixing elements, spargers, static mixing elements, eductors, and lances.

The outlet expanding section 454 is an inverted, truncated cone with an inlet diameter of 1,219 mm (4 ft), an outlet diameter of 5,517 mm (18.1 ft), an overall length of 2,149 mm (7.05 ft), and an included angle of 90 degrees. Optionally, expanding section 454 comprises a plurality of separable segments, or staves, each with a geometry selected to allow easy passage of the staves through an access manway (not shown) on the shell wall of open interstage region 450. The use of such separable segments may improve maintenance access within the open interstage region and may reduce the need to use separable connections at interfaces 445 and 455.

The second reaction stage 460 has a length of 4,500 mm (14.76 ft) and contains a plurality of tubes, represented generally in the figure as 465a, 465b, 465c. The entrance end of each tube in the second reaction stage is attached, for example by welding or rolling, to the R2 inlet tubesheet (not shown per se, but located at the same position in the figure as interfacial connection 455). The exit end of each tube section 465a, 465b, 465c, is attached, for example by welding or rolling, to the R2 exit tubesheet (not shown per se, but located at the same position in the figure as separable connection 475). The R2 inlet tubesheet is 5,517 mm (18.1 ft) in diameter and comprises 22,000 tubes. The layout of the R2 inlet tubesheet is the same as the R1 inlet tubesheet. The tubes within the second reaction stage have an internal diameter of 22.3 mm (0.878 in) and an external diameter 26.9 mm (1.060 in). The tubes are arranged on a 60-degree triangular pattern, with a 34 mm (1.34 in) tubesheet pitch, resulting in a distance between the tubes of 7 mm (0.275 in). Thus, in the embodiment illustrated in FIG. 4, the number, diameter, and placement of the tubes of the second reaction stage (the R2 tubes) is the same as that of the tubes in the first reaction stage (the R1 tubes).

In this embodiment, the first reaction stage (R1) catalyst and the second reaction stage (R2) catalyst are both retained in their respective reactor tubes using catalyst support grid panels comprising wire mesh. Each of the R1 tubes are loaded with 1.295 kg of ACF7 catalyst and each of the R2 tubes are loaded with 1.962 kg of ACS7 catalyst, resulting in a 1.52 catalyst mass ratio.

Although not shown in FIG. 4, this embodiment of the inventive SSOI reactor further may comprise three independently controlled coolant circulation systems, which provide the capability to individually adjust the temperature of each cooled section (410, 430, 460) as needed. HITEC® heat transfer salt, available from Coastal Chemical Co. of Houston, Tex. USA, is used as the coolant medium for all three circulation systems in this embodiment. The systems are herein referred to as the R1 salt circulation system, supporting the first reaction stage 410; the ISHX salt circulation system, supporting the interstage heat exchanger 430; and the R2 salt circulation system, supporting the second reaction stage 460.

Consistent with the design of the present invention, such a coolant system configuration may allow the process-side temperature of interstage heat exchanger to be controlled independently of the process temperature of the first reaction stage, ensuring that the process gas leaving the ISHX can be maintained, for example, at a temperature of at least 240° C.

and not more than 280° C. Although not an essential feature of the inventive design, this specific embodiment also provides the capability of controlling the process-side temperature of the second reaction stage independently of the process temperature of the interstage heat exchanger. Other features of the shell-side salt circulation systems, including system equipment and shellside baffles, are consistent with the previously described embodiment of FIG. 1b. It should be noted that the coolant flows of the present embodiment, moving generally in a direction that is equivalent to the process flow—that is, salt flowing upward through the shell while the process gas also flows upward through the tubes—is commonly referred to as a co-current coolant circulation. It is possible to configure the coolant flow of this embodiment to flow generally downward in a counter-current coolant circulation, or even as a "hybrid" coolant circulation. In at least one embodiment of the present disclosure, the use of co-current coolant circulation is used.

In operation of this exemplary embodiment, the feed gas mixture enters the first reaction stage 410 to produce an R1 exit gas stream comprising acrolein. The R1 exit gas stream is rapidly cooled in the integral interstage heat exchanger 430 to a temperature of between 240° C. and 280° C. and then passed through the uncooled bed of high surface area inert ceramic foam 451. The cooled and filtered R1 exit gas then enters the contracting section 452 of the venturi-mixer. Supplemental oxidant supply line 446 continuously provides a supplemental oxidant stream, comprising air and water vapor, to heat exchanger 447 wherein the supplemental oxidant stream is brought to a temperature of about 260° C. before it is transferred to intermediate throat section 453. In throat section 453, blending elements (not shown) rapidly mix the supplemental oxidant stream with the R1 exit gas to form an oxygen-enriched R2 feed stream at a temperature of between 240° C. and 280° C. The oxygen-enriched R2 feed stream then passes through the expanding section 454 of the venturi-mixer and is distributed to the tubes of the second reaction stage for further conversion to acrylic acid.

The feed gases for this embodiment are described in Table 7A (see "Case 2" on right hand side of table), along with those for the embodiment of FIG. 1a (see "Case 1" on left hand side of table). Note that chemical grade propylene is used as the primary hydrocarbon feed in both of these embodiments (herein denoted by "C3"), which comprises 90% propylene molecules. Table 7A illustrates how operation of the inventive SSOI reactor with the supplemental oxidant addition feed of this embodiment can increase propylene rate, and therefore reactor productivity, by at least 10%.

TABLE 7A

|  | Case 1 SSOI REACTOR | Case 2 SSOI REACTOR with SUPPLEMENTAL OXIDANT |
|---|---|---|
| R1 Propylene:air mole ratio | 0.100 | 0.122 |
| R1 Water:air mole ratio | 6.367 | 0.367 |

TABLE 7A-continued

| | First Reaction Stage feed gas | | | |
|---|---|---|---|---|
| | MSCFH | Nm³/hr | MSCFH | Nm³/hr |
| C3 feed | 194.8 | 5,219 | 214.28 | 5,741 |
| Air feed | 1,757.4 | 47,084 | 1,581.65 | 42,375 |
| Water feed | 645.2 | 17,285 | 580.66 | 15,557 |
| Total Flow | 2,597.4 | 69,588 | 2,376.59 | 63,973 |
| R1 propylene concentration (mole %) | | 6.75 | | 8.11 |

| | Interstage Region (Supplemental Oxidant) feed gas | | | |
|---|---|---|---|---|
| | MSCFH | Nm³/hr | MSCFH | Nm³/hr |
| C3 feed | 0 | 0 | 0 | 0 |
| Air feed | 0 | 0 | 175.74 | 4,708 |
| Water feed | 0 | 0 | 64.52 | 1,729 |
| Total Flow | 0 | 0 | 240.36 | 6,437 |
| Propylene rate | 19,400 lb/hr | 8,820 kg/hr | 21,344 lb/hr | 9,702 kg/hr |

Figure 5:
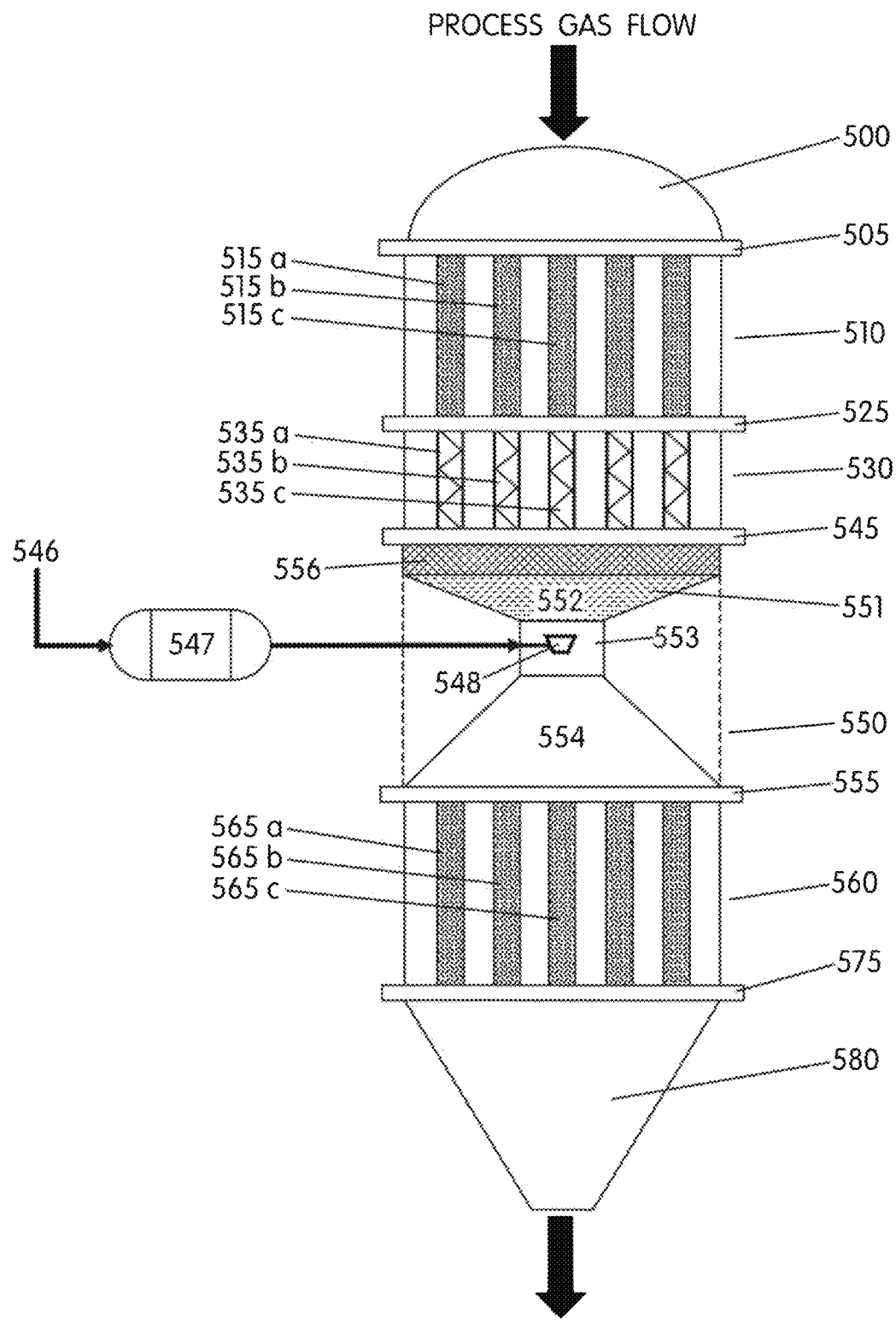
FIG. 5 is a side view representing the tubeside (process) features for another embodiment of an SSOI reactor comprising mixing means for supplemental oxidant addition.

FIG. 5 represents a further embodiment of the inventive Single Shell Open Interstage (SSOI) reactor design comprising means for supplemental oxidant addition to the interstage region of the reactor.

Feed gases (e.g., propylene, steam, oxygen, and nitrogen) enter the reactor from the top, flow vertically downward through the reactor, and exit the reactor at the bottom. This arrangement is a downflow process configuration.

Major sections of the reactor include the domed inlet head 500, the first reaction stage 510 (also referred to herein as "R1"), the interstage heat exchanger 530 (also referred to herein as "ISHX"), the open interstage region 550, the second reaction stage 560 (also referred to herein as "R2"), and the conical outlet head 580.

The interfacial connections between adjacent sections, identified in the figures as 505, 525, 545, 555, and 575, may comprise permanent (e.g., welded) connections or may optionally comprise separable connections, such as flanged connections secured with a plurality of fasteners, such as for example bolts or clamps. In the embodiment of FIG. 5, interfaces 505 and 575 are separable connections, allowing inlet head 500 and conical outlet head 580 to be easily removed for catalyst replacement; further, in at least one embodiment, at least one of interfaces 545 and 555 are also separable connections, thereby providing improved maintenance access to components within the open interstage region 550. Interface 525 can be a welded connection.

The first reaction stage 510 contains a plurality of 22.3 mm (0.878 in) internal diameter tubes, represented generally in the figure as 515a, 515b, 515c. The entrance end of each of these tubes is attached, for example by welding or rolling, to the R1 inlet tubesheet (not shown per se, but located at the same position as separable connection 505). The interstage heat exchanger 530 also contains a plurality of 22.3 mm (0.878 in) internal diameter tubes, generally represented in the figure as 535a, 535b, 535c, and equivalent in number, diameter, and placement to the tubes of the first reaction stage. The exit end of each ISHX tube segment 535a, 535b, 535c, is attached, for example by welding or rolling, to the ISHX tubesheet (not shown per se, but located at the same position in the figure as interfacial connection 545).

The tubes of the interstage heat exchanger are coaxially continuous with the R1 tubes of the first reaction stage, meaning that tube segment 535a is the lower end of tube 515a, tube segment 535b is the lower end of tube 515b, tube segment 535c is the lower end of tube 515c, and so on. As previously noted, such direct connection of the interstage heat exchanger to the shell and tubes of the first reaction stage is referred to herein as an integrated interstage heat exchanger.

High void fraction, turbulence inducing inserts can be placed within the tube segments (535 a, b, c) of the interstage heat exchanger to enhance heat transfer without the accumulation foulants.

The R1 shellside coolant circulation is separated from the ISHX shellside coolant by an interstage baffle (not shown per se, but located at the same position in the figure as connection 525); each of the coaxially continuous tubes extending from the R1 inlet tubesheet to the ISHX exit tubesheet must pass through this interstage baffle. As previously described, the interstage baffle differs from a true tubesheet in that there are no tube-to-baffle welds; instead, the perforations through the interstage baffle are of a slightly larger internal diameter than the outside diameter of the tubes (515 a, b, c), such that a small annular gap (not shown) of between 0.25 and 2.5 mm wide is formed around each tube. The R1 shellside coolant circulation may be arranged in a co-current or in a counter-current configuration; similarly, the ISHX shellside coolant circulation may be arranged in a co-current or in a counter-current configuration as well, and need not match the configuration of the R1 shellside coolant circulation.

In this specific embodiment, the open interstage region 550 contains no tubes and has a total length of about 6,170 mm (20.25 ft). In accordance with the SSOI reactor design of the present invention, the open interstage region can be at least partially filled with one or more stable, high surface area inert materials 551 and 556, in a quantity sufficient to provide at least 930 m$^2$ (10,000 sq ft) of total surface area for removal of foulants, preferably at least 2,790 m$^2$ (30,000 sq ft), and most preferably 3,720 m$^2$ (40,000 sq ft). In this embodiment, the selected stable, high surface area inert material 556 is 20 ppi ("pores-per-inch") ceramic foam tiles, of generally rectangular shape and having a relative density of 8%, a void fraction of 92%, and an effective surface area of about 1,260 m$^2$/m$^3$ (384 ft$^2$/ft$^3$). The ceramic foam tiles are placed in direct contact with the ISHX exit tubesheet (545) and arranged in such a way as to attain a continuous ceramic foam bed with a planar top surface and a uniform thickness of 76 mm (3 in). It is preferred that this ceramic foam bed is secured in place using catalyst support grid panels comprising wire mesh, although other securing means may be optionally used. As configured in this embodiment, such a ceramic foam bed provides a total surface area of more than 2,290 m$^2$ (24,650 sq ft) for removal of foulants.

Within the open interstage region 550 and immediately downstream of the ceramic foam bed is a supplemental oxidant mixing assembly; in this embodiment, the specific mixing assembly is a "venturi-mixer", but other supplemental oxidant mixing assemblies may also be utilized without deviating from the spirit of the present invention.

Supplemental oxidant supply line 546 provides supplemental oxidant, comprising oxygen and optionally one or more inerts, such as for example nitrogen, water, or carbon dioxide, as a gas stream into the venturi-mixer. Optional oxidant heat exchanger 547 may be used to adjust the temperature of the supplemental oxidant before it reaches the venturi-mixer. Optional flow control means, such as for example a flow control valve (not shown) may also be present in supplemental oxidant supply line 546.

The venturi-mixer of this embodiment comprises three sections, interconnected to form a continuous, flow-through mixing assembly: an inlet contracting section 552, an intermediate throat section 553, and an outlet expanding section 554. The overall length of the venturi-mixer is 6,096 mm (20 ft).

The inlet contracting section 552 is an inverted, truncated cone with an inlet diameter of 5,486 mm (18 ft), an outlet diameter of 305 mm (12 in), an overall length of 1,494 mm (4.9 ft) and an included angle of 120 degrees. In this embodiment, additional stable, high surface area inert material 551 is placed within inlet contracting section 552; specifically, contracting section 552 is completely filled with 25.4 mm (1 in) diameter EnviroStone 66 inert ceramic spheres, which provides an additional 1,769 m$^2$ (19,000 sq ft) of surface area for removal of foulants. When combined with the 20 ppi ceramic foam layer adjacent to the ISHX tubesheet, this results in a total surface area within the open interstage region 550 of over 4,060 m$^2$ (43,700 sq ft). A horizontal wire mesh screen (not shown) is also placed at the intersection of contracting section 552 and throat section 553 to support the inert spheres and prevent them from entering throat section 553.

The intermediate throat section 553 is a cylinder with an internal diameter of 305 mm (12 in) and an overall length of 1,219 mm (4 ft); this throat section may comprise one or more blending elements 548 selected from the list including nozzles, injectors, gas-gas mixing elements, distributors, aspirators, coanda-effect mixing elements, spargers, static mixing elements, eductors, and lances. Other than blending elements, it is preferred that throat section 553 be free of obstructions such that mixing efficiency is maximized, e.g., in at least one embodiment, throat section 553 does not comprise stable, high surface area inert material.

In this specific embodiment, blending element 548 comprises a gas-gas mixing element. One example of a suitable gas-gas mixing element is disclosed in EP1726355 (B1). Other examples of suitable gas-gas mixing elements include commercially-available elements, such as the OXYNATOR™ (available from Air Liquide of Paris, France) and the OXYMIX™ Oxygen Injector (available from Linde Gas Division of Linde AG, Hollriegelskreuth, Germany).

When a gas-gas mixing element is used as the blending element, the element can be placed near the upstream end of throat section 553, such that there is at least 3 pipe diameters of unobstructed length downstream of the element. Thus in this embodiment, blending element 548 is placed at a distance of not more than 305 mm (12 in) from the upstream end of throat section 553.

The outlet expanding section 554 is a truncated cone with an inlet diameter of 305 mm (12 in), an outlet diameter of 5,486 mm (18 ft), an overall length of 3,377 mm (11.1 ft), and an included angle of 75 degrees. Expanding section 554 is empty, i.e., it does not comprise stable, high surface area inert material.

Optionally, at least a portion of the shell wall of open interstage region 550 comprises removable shell segments, as indicated by the dotted lines in FIG. 5. In one embodiment, the removable shell segments extend from interface 545 to 555, providing sufficient access to remove one or more complete sections (552, 553, or 554) of the venturi-mixer from open interstage region 550. In another embodiment, the shell wall of open interstage region 550 can be completely removed from the reactor, providing sufficient clearance to remove all three sections of the venturi-mixer simultaneously. The use of such optional removable shell segments may reduce the need for access manways on the shell wall of open interstage region 550.

The second reaction stage 560 contains a plurality of 31.75 mm (1.25 in) internal diameter tubes, represented generally in the figure as 565a, 565b, 565c. The entrance end of each tube in the second reaction stage is attached, for example by welding or rolling, to the R2 inlet tubesheet (not shown per se, but located at the same position in the figure as interfacial connection 555). The exit end of each tube section 565a, 565b, 565c, is attached, for example by welding or rolling, to the R2 exit tubesheet (not shown per se, but located at the same position in the figure as separable connection 575). In this embodiment, the number and diameter of the tubes of the second reaction stage (the R2 tubes) differs from that of the tubes in the first reaction stage (the R1 tubes).

Although not shown in FIG. 5, this embodiment of the inventive SSOI reactor further comprises three independently controlled coolant circulation systems, which provide the capability to individually adjust the temperature of each cooled section (510, 530, 560) as needed. The systems are herein referred to as the R1 coolant circulation system, supporting the first reaction stage 510; the ISHX coolant circulation system, supporting the interstage heat exchanger 530; and the R2 coolant circulation system, supporting the second reaction stage 560. In at least one embodiment, Syltherm™ heat transfer fluid (available from Dow Chemical Co. of Midland, Mich. USA) is used as the coolant medium for all three circulation systems.

Consistent with the design of the present invention, such a coolant system configuration allows the process-side temperature of interstage heat exchanger to be controlled independently of the process temperature of the first reaction stage, ensuring that the process gas leaving the ISHX can be maintained at a temperature of at least 240° C. and not more than 280° C. Although not an essential feature of the inventive design, this specific embodiment may also provide the capability of controlling the process-side temperature of the second reaction stage independently of the process temperature of the interstage heat exchanger, such additional capability to control the oxidation process operation is used in at least one embodiment of the present invention. Other features of the shell-side salt circulation systems, including system equipment and shellside baffles, are consistent with the previously described embodiment of FIG. 1b. It should be noted that the coolant flows of the present embodiment, moving generally in a direction that is opposite to the process flow—that is, coolant medium flowing upward through the shell while the process gas also flows downward through the tubes—is commonly referred to as a counter-current coolant circulation. It is also feasible to configure the coolant flow of this embodiment to flow generally downward in a co-current coolant circulation, or even as a "hybrid" coolant circulation, wherein some coolant flows are co-current while others are counter-current. Additionally, it is envisioned that in some embodiments it may be advantageous to utilize more than one coolant medium for a single reactor, such as for example, Syltherm™ heat transfer fluid in the R1 coolant circulation system and the ISHX coolant circulation system, and HITEC™ salt in the R2 coolant circulation system.

When operated under the supplemental oxidant addition conditions summarized in Case 2 of Table 7A, the reactor of this embodiment has a nominal acrylic acid capacity of 110 kT per year. Also, the interstage residence time for this embodiment, being the sum total of the residence time through the interstage heat exchanger, the ceramic foam layer, and each section of the venturi-mixer, is determined to be 2.56 seconds. Example 7 (below) illustrates how the interstage residence time is calculated for SSOI reactors operated with supplemental oxidant addition.

Figure 6:
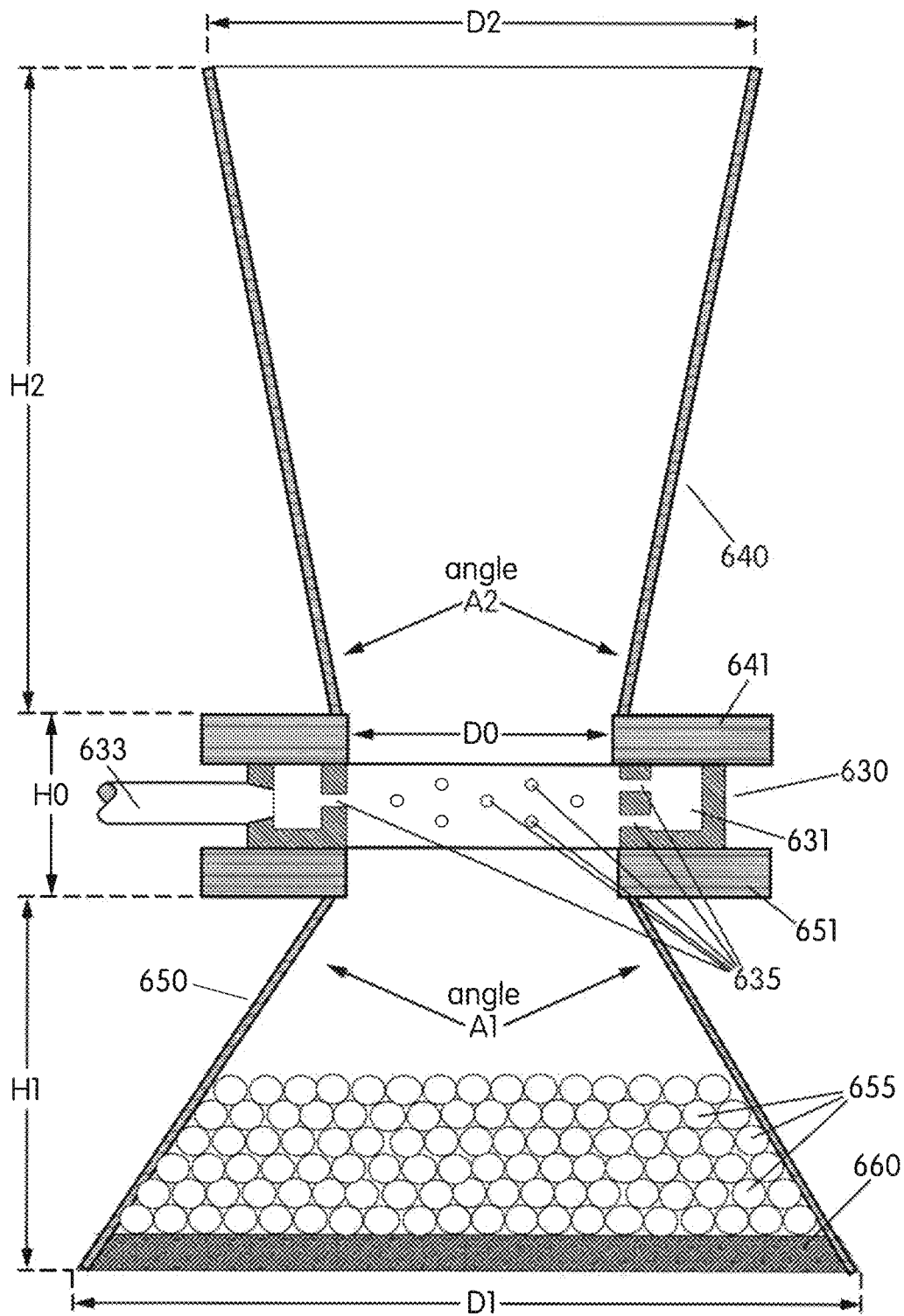
FIG. 6 is a cross-sectional side view of a venturi-mixer for supplemental oxidant addition.

FIG. 6 provides a detailed view of one embodiment of a supplemental oxidant mixing assembly, useful in SSOI reactors operated with supplemental oxidant addition. In this embodiment, the supplemental oxidant mixing assembly is a venturi mixer comprising a novel injector ring, and said venturi mixer is shown in a process upflow orientation, wherein process gases enter from the bottom through inlet contracting section 650, pass through intermediate throat section 630, and exit through outlet expanding section 640. Such an orientation may be useful in process upflow reactors, such as for example the reactor embodiment of FIG. 4. Although described herein in a process upflow orientation, it should be noted that the venturi mixer apparatus of FIG. 6 could also be beneficially employed in a downflow orientation.

In this embodiment, the venturi mixer rests upon a 150 mm thick (6 in) layer of stainless steel open cell foam 660. Inlet contracting section 650 is conical in shape, with a base dimension D1 of 5517 mm (18.1 ft), a height H1 of 379 mm (1.24 ft), and an included angle A1 of 160 degrees. Section 650 further comprises mounting flange 651, which is about 76 mm (3 in) thick. In at least one embodiment, the interior volume of inlet contracting section comprises a particulate inert material having a bulk void fraction of less than 50%. In one embodiment, for example, 50% of the interior volume of inlet contracting section 650 is occupied with 25.4 mm (1 in) diameter Denstone 57 inert spheres (represented in the figure as 655) to reduce residence time in this section of the venturi mixer.

Intermediate throat section 630 is cylindrical, with an internal diameter D0 of 1,219 mm (4 ft). Section 630 has overall height H0 of 457 mm (1.5 ft), which results from a 305 mm (12 in) thick wall section in combination with a pair of 76 mm (3 in) mounting flanges 641 and 651; mounting flanges 641 and 651 provide a separable connection to section 630 and are held in place with removable fasteners (not shown), such as for example bolts. The interior of throat section 630 comprises an integral annular channel 631 which is in fluidic connection with a plurality of injector ports 635 and is herein referred to as an "injector ring"; injector ports 635 are the blending elements of the injector ring and serve to uniformly distribute the supplemental oxidant stream throughout the throat section of the venturi mixer apparatus.

In the embodiment of FIG. 6, the injector ring employs a total of 216 injector ports, each 9.5 mm (⅜ in) in diameter. As indicated in the figure, these injector ports are configured into three parallel rows, placed in a regular triangular/staggered pattern along the interior surface of the injector ring. Each row contains 72 injector ports, evenly spaced around the interior circumference of the injector ring, with a distance of about 44 mm (1.7 in) between each port in the row. At least one Supplemental Oxidant supply line 633 is connected to throat section 630, providing a path for supplemental oxidant feed gas to enter annular channel 631. In this embodiment, supplemental oxidant supply line 633 is 203 mm (8 in) in diameter and comprises means for temperature control, such as an optional upstream temperature control heat exchanger (not shown), and also means for flow control, such as an upstream flow control valve (not shown). In at least one embodiment, the diameter of supply line 633 is large relative to the size of the injector ports 635 to enhance distribution of the feed gas around the entire circumference of the injector ring; for example, the ratio of supply line 633 diameter to injector port 635 diameter can be at least 10, such as at least 15 or at least 20. In this specific embodiment, the supply line diameter is 203 mm and the injector port diameter is 9.5 mm, making the ratio of supply line 633 diameter to injector port 635 diameter 21. This large ratio also assures sufficient pressure drop to resist backflow of potentially flammable process gases from the injector ring into supplemental oxidant supply line 633. Optional filtration of the supplemental oxidant gas stream may also be employed to minimize potential blockage of small diameter injector ports with undesired material, such as for example polymeric solids, rust particles, or entrained liquid droplets.

Outlet expanding segment 640 may be conical in shape, with a base dimension D2 of 5517 mm (18.1 ft), a height H2 of 2149 mm (7 ft), and an included angle A2 of 90 degrees. Segment 640 further comprises mounting flange 641, which is about 76 mm (3 in) thick. In at least one embodiment, the interior volume of outlet expanding segment 640 is empty.

When the supplemental oxidant mixing assembly of this embodiment, which includes the aforementioned Denstone spheres in contracting segment 650, is installed in an SSOI reactor of the type previously illustrated in FIG. 4, and is further operated under the conditions of Table 7A, Case 2 (e.g., a propylene rate of 9,702 kg/hr and a total supplemental oxidant flow of 6,437 Nm³/hr), the resulting SSOI reactor will operate with an interstage residence time of about 2.5 seconds and will have more than 4,850 m² (52,300 sq ft) of inert surface area within the interstage region.

Combining the SSOI reactor of the present invention with an acrylic acid collection and purification system may result in an improved process for making commercial purity acrylic acid. For example, a counter-current absorption tower provided with an absorbent liquid stream, such as for example water or diphenyl, may be used to collect acrylic acid from the reactor product gas, thereby forming a crude product solution comprising acrylic acid and absorbent. Acrylic acid may then be recovered from the crude product solution using separations steps such as solvent extraction and azeotropic distillation. Examples of such absorption-based acrylic acid collection and purification systems are provided in U.S. Pat. Nos. 5,426,221; 6,639,106; and 6,998,505.

Figure 8:
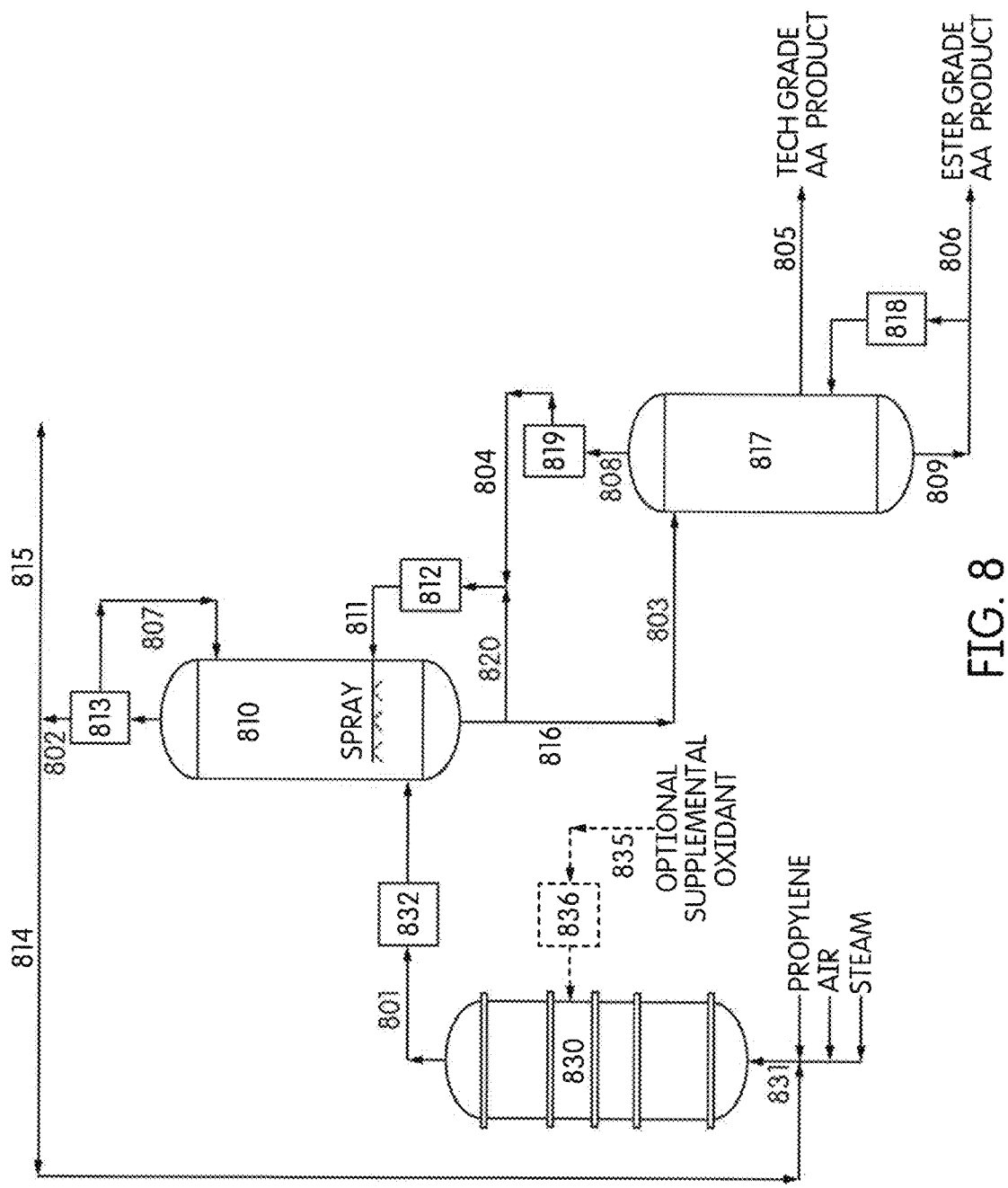
FIG. 8 is one embodiment of an integrated process for making acrylic acid, comprising the SSOI reactor of the present invention and a solvent-free acrylic acid collection and purification system.

FIG. 8 shows one embodiment of the present invention relating to an integrated process for making acrylic acid, comprising an upflow SSOI reactor (830) and a solvent-free acrylic acid collection and purification system. The solvent-free acrylic acid collection and purification system comprises a dehydration column and a finishing column.

The large-scale commercial SSOI reactor of this specific embodiment has a nameplate acrylic acid capacity of 160 kT/year and the solvent-free acrylic acid collection and purification system, herein referred to as a "SFT" system, is sized to provide an equivalent (matched) acrylic acid processing capacity. An example of an SFT system is disclosed in U.S. Pat. No. 8,242,308, which is herein incorporated by reference. The use of a SFT system in combination with the SSOI reactor of the present invention may provide at least one of the following benefits over the combination of the SSOI reactor with more traditional absorber-based acrylic acid collection and purification processes:

(1) The SFT system comprises no absorption tower, and consequently does not require the addition of absorbents, such as for example liquid streams comprising diphenyl or water (2) The SFT system is capable of dehydrating crude acrylic acid without the use of extraction solvents, such as ethyl acrylate, or distillation solvents which form azeotropic mixtures with water, such as for example methyl isobutyl ketone (MIBK), ethyl acetate, toluene, or isopropyl acetate.

Such improvements may vastly simplify the production of acrylic acid and reduce the quantity of process equipment required, thereby resulting in significant operational and capital cost savings over prior art processes.

Referring to FIG. 8, reactor 830 is constructed with removable inlet and outlet reactor heads. At design conditions, propylene is provided to the reactor at a flow rate of over 14,100 kilograms per hour (31,000 pounds per hour). Propylene, Air, Recycle Gas (stream 814), and optionally steam, are blended together using in-line static mixing elements to form a mixed feed gas with a propylene concentration of at least 7.5 mol/%, a molar ratio of oxygen-to-propylene of between 1.6 and 2.0, and a molar ratio of water vapor-to-propylene of about 1.2 or less. In one embodiment, the mixed feed gas has a propylene concentration of at least 8 mol %, and the molar ratio of oxygen-to-propylene is about 1.8, and the molar ratio of water vapor-to-propylene is about 0.75 or less.

The mixed feed gas enters the bottom of the reactor via common feed line 831 at a temperature greater than the dewpoint temperature of the mixture. In one embodiment, the mixed feed gas enters the reactor at a temperature of less than about 200° C., for example about 195° C. or even about 145° C. One or more heat exchangers and propylene vaporizers (not shown) may optionally be used to control the temperature of the individual feed gases, thereby controlling the temperature of the mixed feed gas entering the reactor. Optionally, the temperature of recycle gas stream 814 may be controlled through the exchange of heat with Product gas stream 801; heat exchange apparatus 832 may be configured for this purpose (not shown). The first reaction stage, which is in the lower portion of the reactor, comprises over 33,000 seamless carbon steel tubes of 25.4 mm internal diameter, arranged on a 60-degree triangular pattern, and has a length of 3,750 mm (12.3 ft). Each tube within the first reaction stage is coaxially continuous with the tubes of the interstage heat exchanger, located immediately downstream of the first reaction stage and referred to herein as an integrated interstage heat exchanger. Thus, the interstage heat exchanger (ISHX) also comprises over 33,000 seamless carbon steel tubes of 25.4 mm internal diameter. The ISHX has a length of 2,100 mm (6.9 ft). The total length of the continuous tubes passing through both the first reaction stage and the interstage heat exchanger is therefore 5,850 mm (19.2 ft). To retain catalyst within these continuous tubes, a plurality of the previously described catalyst support grid panels comprising wire mesh are directly attached to the first stage inlet tubesheet. Each of the continuous tubes is then loaded as follows, beginning with the upstream (entrance) end of the tube:

250 mm (10 in) of ¼ in (6 mm) diameter EnviroStone 66 inert ceramic spheres
730 mm (29 in) of ACF7-L (large cylinder) catalyst
2770 mm (109 in) of ACF7-S (small cylinder) catalyst
a 2100 mm (83 in) long twistee turbulence inducing insert This loading schedule results in a charge of 1.042 kg of total ACF7 catalyst (large+small size particles) in each first reaction stage tube. The residence time of the process gas through the interstage heat exchanger is about 0.94 seconds.

The process gases leave the interstage heat exchanger at a temperature of not more than about 280° C. (536° F.) and then pass through the open interstage region. Optional supplemental oxidant 835, such as air or other oxygen-containing gases, may be passed through optional heat exchanger 836 and then added to the open interstage region; in such cases, optional mixing devices, such as for example a venturi mixer of the type previously described herein and further illustrated in FIG. 6, may be used to safely homogenize the mixture of process gas and supplemental oxidant. In this specific embodiment, however, supplemental oxidant is not added to the open interstage region.

The open interstage region is 2,100 mm long (6.9 ft) and is loaded with sufficient 38 mm (1.5 in) diameter EnviroStone 66 inert spheres to occupy about 90% of the volume within the open interstage region, thereby providing a bed of ceramic spheres with an average depth of over 1,895 mm (6.2 it) and more than 4,180 m$^2$ (more than 45,000 sq ft) of surface area for removal of foulants. Additionally, the interstage residence time (ISHX and open interstage region residence times combined), as measured at the reference conditions of 240° C. and 30 psia (2 atm), is about 2.2 seconds, i.e., less than 3 seconds residence time.

Process gases then pass into the second reaction stage, located in the upper portion of the reactor. The second reaction stage has a length of 3,405 mm (11.2 feet). The second reaction stage has a tube count, internal tube diameter, and tube layout equal to that of the first reaction stage, thereby also comprising over 33,000 seamless carbon steel tubes of 25.4 mm internal diameter, arranged on a 60-degree triangular pattern. To retain catalyst within these tubes, a plurality of the previously described catalyst support grid panels comprising wire mesh are directly attached to the second stage inlet tubesheet. Each of these tubes is loaded as follows, beginning with the upstream (entrance) end of the tube:
- a modified twistee insert of 305 mm (12 in) overall length, comprising a 25.4 mm (1 in) long conical retaining spring attached to the upstream end of a 280 mm (11 in) long twistee turbulence inducing insert
- 640 mm (25 in) of ACS7-L (large sphere) catalyst
- 2260 mm (89 in) of ACS7-S (small sphere) catalyst
- 200 mm (7.9 in) of ¼ in (6 mm) diameter EnviroStone 66 inert ceramic spheres This loading schedule results in a charge of 1.417 kg of total ACS7 catalyst (large+small size particles) in each second reaction stage tube, and provides an overall 1.36 Catalyst Mass Ratio for the reactor.

All three primary reactor regions (first reaction stage, interstage heat exchanger, and second reaction stage) may be cooled by their own independent, shell-side coolant circulation systems. One or more of Dowtherm™, Syltherm™, or HITEC® salt may be used as the cooling medium; in this specific embodiment, molten HITEC® cooling salt is employed. Although not specifically shown in the figure, each of these coolant circulation systems comprises other components, such as for example pumps, coolant flow control valves, and steam boilers, and operates in a co-current circulation configuration, meaning that, for each reactor region, a stream of cool salt enters the lower portion of the region and a stream of warm salt exits the upper portion of the region.

Product gas comprising acrylic acid 801 leaves the top of the reactor and is cooled in indirect heat exchanger 832 to a temperature of about 225° C. (437° F.). Indirect heat exchanger 832 may comprise one or more heat transfer apparatus, including but not limited to shell-and-tube heat exchangers, jacketed tubes, plate heat exchangers (PHE's), twisted tube heat exchangers, and spiral heat exchangers. In this embodiment, heat exchanger 832 is a shell-and-tube heat exchanger. In an alternative embodiment, indirect heat exchanger 832 is omitted and the SSOI reactor comprises an integral exit cooler (not shown), situated between the outlet (top) tubesheet of the second reaction stage and the outlet reactor head. Such an integral exit cooler is similar in design to the interstage heat exchanger, having tubes which are coaxially continuous with the tubes of the second reaction stage, an independent coolant circulation, and high-void fraction turbulence inducing inserts within each tube.

Cooled product gas then enters the lower portion of dehydration column 810, where it is directly contacted by a circulating liquid spray. A liquid dehydration bottoms stream 816 is removed from the bottom of column 810 and a portion of the stream (820) is transferred to reboiler 812, which may comprise one or more thermosiphons or forced-circulation type reboilers. The heated stream is then supplied (via transfer line 811) to the spray apparatus within the lower portion of dehydration column 810; such a dehydration column configuration is known herein as an "integrated quench" step. In an alternative embodiment, this liquid contact quench step is performed in one or more vessels (not shown) immediately upstream of dehydration column 810; such an alternative embodiment is referred to as a "staged quench" step.

In the embodiment of FIG. 8, following contact with the liquid spray within the dehydration column, the quenched process gas then passes upward through a series of separation-stage components, such as, for example, one or more of sieve trays, dual-flow trays, bubble cap trays, loose-fill packing, valve trays, and structured packing, to separate acrylic acid from light ends impurities. An intermediate process gas stream, comprising water vapor and noncondensable gases, such as, for example, nitrogen, carbon dioxide, propane, and unreacted propylene, exits the top of column 810 and passes through condenser 813, generating condensate 807 which is refluxed back into column 810, and a dehydration column overhead vapor stream 802 comprising water vapor and noncondensable gases. In one embodiment, dehydration column overhead vapor stream 802 comprises less than 25 mol % water vapor. In one embodiment, stream 802 comprises about 80% nitrogen and not more than 5% combined $CO_2$ and CO. Dehydration column overhead vapor stream 802 is divided into two portions, a recycle gas stream 814 and a purge stream 815. Recycle gas stream 814 has a mass flow rate of between 5 and 50% of the mass flow rate of overhead vapor stream 802, such as, for example, between 10 and 40% of overhead vapor stream 802, or between 15 and 35% overhead vapor stream 802. Recycle gas stream 814 is returned to SSOI reactor 830. Optionally, recycle gas stream 814 may be processed in one or more conditioning steps, such as for example filtering, coalescing, preheating, and compressing (not shown) before being returned to reactor 830. If compressors are used, it is preferred that at least one of said compressors be of the type selected from the list including blowers (also known in the art as radial compressors or centrifugal compressors), oil-free screw compressors, and liquid jet ejector compressors. In one embodiment, recycle gas stream 814 is first blended with process air and then processed in a centrifugal compressor prior to returning to SSOI reactor 830. In at least one embodiment, the interior surfaces of the process lines through which recycle gas stream 814 flows are maintained at a temperature of not less than about 90° C., and above the dewpoint of water, to prevent condensation of water vapor therein. Purge stream 815 may vented or, in at least one embodiment, it may be further processed, for example, in one or more of a catalytic combustion unit (CCU), a thermal oxidizer, and a waste heat recovery system (not shown).

Stream 803, the portion of the liquid dehydration bottoms stream 816 not transferred to reboiler 812, is provided to finishing column 817. Finishing column 817 operates at subatmospheric pressure and comprises a series of separation-stage components, such as, for example, one or more of sieve trays, dual-flow trays, bubble cap trays, loose-fill packing, valve trays, and structured packing, to separate acrylic acid from heavy ends impurities and produce side-draw acrylic acid product stream 805. Side draw acrylic acid stream 805 comprises at least 99.5% acrylic acid by weight, less than 0.15% water, and less than 0.075% acetic acid; thus the stream meets purity specifications for "Technical Grade Acrylic Acid" and may be used without further purification for this purpose. Optionally, side-draw acrylic acid product stream 805 may be further processed in a melt-crystallization process (not shown) to obtain acrylic acid of even higher purity.

Generally, bottoms recirculation 809, comprising heavy ends, such as for example acrylic acid dimer, is circulated through reboiler 818, which may comprise one or more thermosiphon or forced-circulation type reboilers, and returned to the lower portion of the finishing column. At least a portion of the bottoms recirculation 809 is transferred to an ester process (via ester grade product stream 806), such as for example a butyl acrylate production process, comprising a dimer cracker. In one embodiment, the mass flow ratio of ester grade product stream 806 to side-draw acrylic acid product stream 805 is not more than 1.5. In another embodiment, the mass flow ratio of ester grade product stream 806 to side-draw acrylic acid product stream 805 is not more than 1.0. Optionally, a portion of the bottoms recirculation 809 is recycled to the top of the finishing column to reduce polymerization inhibitor consumption. Finishing column overhead stream 808 is passed through total condenser 819; none of the resulting liquid condensate is refluxed to column 817; instead, all of finishing column condensate stream 804 is combined with stream 820 and returned to the spray apparatus within the lower portion of the dehydration column 810.

It is recognized that a substantial number of known additional features and details, such as the use of tracing, insulation, cleaning equipment, instrumentation, in-line filters, multipoint thermocouples, safety equipment, energy recovery equipment, inhibitor spraying and distribution apparatus, and specific materials of construction, as well as the addition of polymerization inhibitors, oxygen-containing gas, antifoulants, and corrosion inhibitors at specific points within the process, may be further incorporated into this process design without detracting from the scope of the present inventive embodiment.

In at least one embodiment, means may be employed for reducing the operating pressure within the second reaction stage. Such means may be used individually, but can also be used in combination with one or more design features, such as the aforementioned use of tubes with internal diameters greater than 22.3 mm. In one embodiment, a conical outlet reactor head (as represented in FIG. 5 by component 580) can be utilized, rather than a domed or elliptical head, to reduce turbulent flow pressure loss at the reactor outlet.

In another embodiment (see FIG. 8), large diameter exit piping 801 can be used to transfer reactor product gas (also known as "reaction gas") between the reactor outlet and downstream collection and purification equipment, such as for example, dehydration tower 810, in order to minimize pressure within SSOI reactor 830. As used herein, the term "large diameter exit piping" means exit piping of sufficient diameter to achieve an outlet diameter ratio, $K_O$, of 0.08 or more. The outlet diameter ratio, $K_O$, is defined herein as the ratio of the diameter of the exit piping ($D_P$) to the diameter of the outlet reactor head ($D_R$)—that is, $K_O=D_P/D_R$. By way of example, for the reactor embodiment of FIG. 1, which has an outlet reactor head diameter of 5,517 mm (18.1 ft), an exit pipe of 305 mm (12 in) diameter would not be considered "large diameter exit piping", because $K_O=0.055$. Therefore, for an embodiment wherein the outlet reactor head diameter is 5,517 mm (18.1 ft), the exit piping from the reactor outlet to the dehydration column would be at least 457 mm (18 in) in diameter (K=0.083), such as, for example, at least 610 mm (24 in) in diameter (K=0.111), at least 762 mm (30 in) in diameter (K=0.138), or at least 914 mm (36 in) in diameter (K=0.166). Similar calculations can of course be performed by one of ordinary skill, given the benefit of this disclosure, to determine appropriate dimensions for other "large diameter exit piping" given a known reactor outlet head diameter.

In some embodiments, an optional heat exchanger, herein referred to as an "R2 exit cooler" is placed downstream of the reactor outlet to adjust the temperature of the product gas prior to its transfer to downstream collection equipment, such as an aqueous absorber or a dehydration tower. Shell and tube type designs are well represented in the prior art for use in R2 exit cooler service (see for example U.S. Pat. No. 7,038,079) and, if used, could be designed to minimize process-gas side pressure drop. Additionally, because fouling of such optional shell-and-tube type R2 exit coolers is common, in at least one embodiment, the process-gas side of the R2 exit cooler can be constructed of materials resistant to fouling, such as for example monel or other copper-containing metals (see for example, U.S. Pat. No. 7,906,679, hereby incorporated by reference). Geometric design features, such as sloping process lines and vertically oriented exchanger tubes may also be beneficial in resisting the accumulation of foulants. The use of liquid phase or vapor phase inhibitors and antifoulants may also be beneficial. Finally, the incorporation of low point drains and continual monitoring of the process-gas side exchanger surfaces for fouling, combined with expeditious removal of any accumulations identified during said monitoring, can help minimize pressure drop increases across the exchanger and help to keep the associated upstream second reaction stage operating pressure from rising.

An alternative to the aforementioned shell-and-tube type R2 exit cooler is a low-pressure drop, liquid-contact heat exchanger, also known as a "spray cooler," which is described in U.S. Pat. No. 8,242,308 (see, e.g., FIG. 2) and herein incorporated by reference. In some embodiments, both a shell-and-tube type R2 exit cooler and a spray cooler can be employed; if both types of exchangers are used in combination with the SSOI reactor of the present invention, in at least one embodiment, the liquid-contact heat exchanger can be placed downstream of the shell- and tube type R2 exit cooler.

EXAMPLES

Example 1—Decoking Trials

It has been reported in the literature that special methods can be employed to "decoke" and/or "regenerate" MMO catalysts, thereby improving their conversion and selectivity. The method generally involves utilizing brief treatment periods of 12 or more hours in which the reactor is taken out of production and the MMO catalysts are exposed to air, or a combination of steam and air, in situ. According to the literature, such treatments can be expected to enhance the oxidation states of the MMO catalysts, remove carbonaceous deposits (via oxidation of same), and reduce process-side pressure drop across the reactor, thereby enhancing performance (see for example, Column 7, lines 33-67, of U.S. Pat. No. 7,897,813). Example 1 was performed to determine if use of those treatment methods might provide benefits when applied to the SSOI reactor of the present invention.

To perform this test, the previously-described SSOI reactor represented in FIGS. 1a, 1b & 1c was loaded with new commercial catalysts. In this particular example, ACF-7 and ACS-7 catalysts were selected for use in the inventive SSOI reactor.

Each tube of the first reaction stage 110 was charged with ACF-7 catalyst. Starting from the tube entrance at the R1 inlet tubesheet, the tubes of the first reaction stage (115 a, b, c) were loaded as follows: about 267 mm of inert spheres, 905 mm ACF-7L catalyst, and 3445 mm ACF-7S catalyst. This resulted in a total mass (ACF-7L+ACF-7S) of 1.295 kg/tube of first stage catalyst.

The remaining 2,057 mm long tube segment (135 a, b, c), which passes through the integral interstage heat exchanger 130, was occupied by a short (25-50 mm deep) transitional layer of inert 5/16" (8 mm) silicon carbide rings (available from Norton Chemical Process Products Corp, Akron Ohio, USA), resting atop a modified twistee insert. As previously described, such a modified twistee insert comprised a 25.4 mm (1 in) long conical catalyst retaining spring (see FIG. 1d) welded to the upstream end of one of the previously described the 2,032 mm (80 in) long twistee inserts. The conical spring had a top external diameter, $d_{TS}$, of 6.1 mm (0.241") and a bottom external diameter, $d_{BS}$ of 19.1 mm (0.75")—equal to the effective diameter of the twistee insert. The conical catalyst retaining spring was fabricated from eleven evenly-spaced coils of 1.47 mm (0.058 in) diameter stainless steel wire to form a conical spring with an overall height ($h_s$) of 25.4 mm (1 in) and coil spacing narrow enough to prevent the silicon carbide rings from passing through. Thus, by attaching the conical catalyst retaining spring to the end of the twistee insert, a transitional layer of rings between 25.4 mm and 51 mm in height was held in place just upstream of the twistee insert. This transitional layer in turn supported the upstream ACF-7S catalyst, holding it within the first stage reaction section and preventing it from occupying the lower ends of the tubes (135 a, b, c) within the interstage heat exchanger. The twistee inserts within the interstage heat exchanger were themselves retained in the ISHX tubes using the previously-described catalyst support grid panels comprising wire mesh.

The open interstage region 150 was loaded with sufficient 1.5 in diameter EnviroStone66 ceramic spheres to fill approximately 93% of the available interstage volume. These spheres were loaded by pouring into the reactor and were allowed to self-assemble into a bed with a void fraction of about 40%. As previously stated, this yielded about 4,400 m² (47,500 sq ft) of surface area for removal of foulants.

Each tube of the second reaction stage 160 was charged with ACS-7 catalyst. Starting from the tube entrance at the R2 inlet tubesheet, the tubes of the second reaction stage (165 a, b, c) were loaded as follows: 200 mm of inert spheres, 800 mm of ACS-7L catalyst, and 3500 mm of ACS-7S catalyst. This results in a total mass (ACS-7L+ACS-7S) of 2.122 kg/tube of second stage catalyst and a 1.64 R2:R1 Catalyst Mass Ratio. The second reaction stage (R2) catalyst is retained in the reactor tubes using the previously described catalyst support grid panels comprising wire mesh.

The SSOI reactor of this example was then operated over a long period with a target propylene feed concentration of between 6.5% and 7.1% by volume, an average feed concentration of 13.6% by volume oxygen, an average feed concentration of 27.7% by volume water, and the balance being inert gases including nitrogen.

After 4,776 elapsed hours of operation, the reactor was taken off-line to perform the first test of the "decoking" or "regenerative" treatment method. The treatment consisted of supplying only air to the reactor at a flow rate of 13,170 m³/hr (465 MSCFH) and a temperature of 224° C. (435° F.). The R1 salt supply temperature ($T_{R1salt}$) was gradually raised over a period of about 9 hours to a maximum of 347° C. (657° F.) and held at this temperature for 21 hours. During this period the R2 salt supply temperature ($T_{R2salt}$) was maintained at 285° C. (545° F.) to protect the R2 catalyst from overheating. During the total 30 hour regeneration period, catalyst temperatures and exiting process gases were monitored. Surprisingly, no exotherm, nor any indication of CO or CO2 formation, (denoting oxidation of carbonaceous solids) was detected. In fact, during the 21 hour period of maximum heating, the difference between the first stage catalyst temperature ($T_{R1cat}$) and the first stage salt supply temperature ($T_{R1salt}$) was essentially zero ($T_{R1salt} - T_{R1cat} \leq 0.33$). When the treatment was complete, the reactor was returned to normal operation. After 24 hours of steady-state operation, no improvement in conversion nor selectivity was evident. Also, no change in the pressure drop across the reactor was detected. It was concluded that there was no removal of carbon deposits, nor any significant regeneration of the MMO catalysts from this treatment method.

After about another 3,400 hours of operation (8,184 elapsed hours of operation), the reactor was again taken off-line to perform a second test treatment. The treatment again consisted of supplying only air to the reactor at a flow rate of 13,170 m³/hr (465 MSCFH) and 224° C. (435° F.). The R1 salt supply temperature ($T_{R1salt}$) was maintained between 350° C. (662° F.) and 365° C. (690° F.) and the R2 salt supply temperature ($T_{R2salt}$) was maintained at 300° C. (572° F.) to protect the R2 catalyst from overheating. During the 21 hour treatment period, there was no evidence of CO or $CO_2$ generation, nor any indication of exothermic reactions. The reactor was returned to normal operation. After 24 hours, no improvement in conversion or selectivity was evident. Also, no change in the pressure drop across the reactor was detected. It was concluded that there was no removal of carbon deposits, nor any significant regeneration of the MMO catalysts from this treatment method.

The air-only treatment was repeated four more times to determine if benefits might be realized after the catalyst had experienced significant Time On-Stream. The results obtained were no different than those of the first two trials. All treatment tests are summarized in Table 1A.

TABLE 1A

| Trial # | Time On-Stream (elapsed hours) | Activity | Duration (hours) |
| --- | --- | --- | --- |
| 0 | 0 | Initial Reactor Start-up/New catalyst | — |
| 1 | 4,776 | Air Treatment | 30 |
| 2 | 8,184 | Air Treatment | 33 |
| 3 | 13,440 | Air Treatment | 21 |
| 4 | 15,480 | Air Treatment | 19 |

TABLE 1A-continued

| Trial # | Time On-Stream (elapsed hours) | Activity | Duration (hours) |
|---|---|---|---|
| 5 | 19,656 | Air Treatment | 16 |
| 6 | 24,048 | Air Treatment | 37.5 |
| 7 | 29,112 | Reactor Shutdown/Catalyst replaced | — |

Additional pressure measurement data for the reactor is summarized in Table 1B. This table compares pressure values within the reactor from the period before performing any regeneration treatments to pressure values within the reactor from the period after completing all the regeneration treatments. The table includes data from two essentially equivalent flowrate conditions during each period.

TABLE 1B

| Average Propene flow m³/hr | Total Process Gas flow m³/hr | Time Period used to calculate average values Time On Stream | | Average Pressure Values bar | | | |
|---|---|---|---|---|---|---|---|
| | | range | | R1 Inlet | Inter-Stage | R2 Outlet | dP In-Out |
| | | start hrs | end hr | | | | |
| Before Trial #1 (First Treatment) | | | | | | | |
| 4,132 | 63,427 | 60 | 72 | 2.23 | 1.87 | 1.22 | 1.01 |
| 2,822 | 43,054 | 3,576 | 3,600 | 1.80 | 1.53 | 1.18 | 0.62 |
| After Trial #6 (Last Treatment) | | | | | | | |
| 4,087 | 57,341 | 25,380 | 25,392 | 2.24 | 1.85 | 1.26 | 0.98 |
| 2,902 | 41,938 | 28,632 | 28,656 | 1.79 | 1.55 | 1.18 | 0.61 |

It is evident from these experimental trials that, for the SSOI reactor of the present invention, no performance improvements result from "decoking" or "regenerative" treatments. This result is surprising given that such treatments appear to provide benefits with other reactor designs, such as tandem and SRS reactors. Without being bound to theory, it is hypothesized that the reason no indication of carbonaceous deposit removal was seen is that the inventive SSOI reactor design effectively prevented the formation of these carbonaceous deposits. This conclusion is further supported by the essentially unchanged reactor pressure profile (Table 1B) over an elapsed operating period of more than 28,000 hours; if significant deposits were accumulating, it would be expected that the pressure drop across the SSOI reactor would have increased significantly over such a long operating period. Finally, when the reactor was taken offline for catalyst replacement, the interior of the reactor was inspected and no significant carbonaceous deposits were found within the interstage heat exchanger nor the open interstage region. Thus, the SSOI reactor design of the present invention clearly performed better than prior art reactor designs, such as for example the reactor of U.S. Pat. No. 7,897,813.

Example 2—Residence Time ISHX+OIS

The previously-described reactor embodiment of FIG. 1 has 22,000 tubes and a nameplate capacity of 100 kTA acrylic acid. It was desired to determine the interstage residence time, as well as the residence time of the process gas flow through the interstage heat exchanger tubes (the ISHX residence time) at design operating rates.

The reactor was designed for operation at a propylene feed rate of 19,400 pph (8,799 kg/hr), an $O_2$:propylene volume ratio of 1.8, and a steam:propylene volume ratio of 3.6. As measured at the reference conditions of 240° C. and 30 psia (2 atm), the total gas flow through the interstage region was about 2,284,360 ft³/hr (64,694 m³/hr).

TABLE 2A

Residence Time within Interstage Heat Exchanger (ISHX) Tubes
22.3 mm I.D. (0.878 in) × 2100 mm (6.9 ft) × 22,000 tubes;
one turbulence inducing insert + conical retaining spring
inserted into each tube

| | | |
|---|---|---|
| Total Volume of empty ISHX Tubes | 638.6 ft³ | 18.1 ft³ |
| Void fraction of Twistee inserts within ISHX Tubes | 0.923 | |
| Available Volume in ISHX Tubes, after deducting volume of inserts | 589.4 ft³ | 16.7 ft³ |
| Effective Space Velocity through ISHX = (2,284,360 ft³/hr)/(589.4 ft³) | 3,876 hr⁻¹ | |
| Equivalent residence time within the ISHX | 0.93 seconds | |

This result of 0.93 seconds was within the targeted SSOI reactor design requirement that the residence time of process gas through the interstage heat exchanger be not more than 1.5 seconds.

TABLE 2B

Residence Time within Open Interstage Region
2,100 mm (6.9 ft) tall × 5517 mm (18.1 ft) in diameter;
volume is filled to a depth of 1,950 mm (6.4 ft)
with 1.5 in diameter EnviroStone 66 inert ceramic spheres (≈93% fill)

| | | |
|---|---|---|
| Total Volume of empty Interstage Region | 1774.5 ft³ | 50.3 m³ |
| Void fraction of inert spheres | 0.40 | |
| Available Volume in Interstage Region, after deducting volume of inert spheres | 784.3 ft³ | 22.2 m³ |
| Effective Space Velocity through Open Interstage Region = (2,284,360 ft³/hr)/(784.3 ft³) | 2,913 hr⁻¹ | |
| Equivalent residence time within the Open Interstage Region | 1.24 seconds | |

Summing the residence times through the ISHX and the open interstage region yielded a combined time of 2.17 seconds, which was defined herein to be the interstage residence time. This result was consistent with the targeted SSOI reactor design requirement that the Interstage Residence Time was not more than 3 seconds.

Example 3—Acetic Acid yield

A pilot plant scale reaction system was used to study the response of oxidation reactors to changes in process variables. The first reaction stage comprised two vertical tubes of 22.1 mm (0.87 in) internal diameter within a common first stage circulating-salt cooling jacket. The tubes in the first reaction stage were charged to a length of 4,191 mm (13.75 ft) with cylindrical ACF R1 catalyst, commercially available from Nippon Shokubai Kagaku Kogyo Co., Ltd of Japan. The second reaction stage comprised three vertical tubes of 22.1 mm (0.87 in) internal diameter within a common second stage circulating-salt cooling jacket. The tubes in the second reaction stage were charged to a length of 2,743 mm (9 ft) with spherical ACS R2 catalyst, also commercially available from Nippon Shokubai Kagaku Kogyo Co., Ltd of Japan. The two reaction stages were connected by a well-insulated interstage pipe, dimensioned to keep the residence time between the two reaction stages at not more than 3 seconds. Process gas flow was configured to enter the top of the first reaction stage, flow downward through the vertical tubes, and exit at the bottom of the first reaction stage; the "S" shaped interstage pipe then directed the process gas flow to the top of the second reaction stage, where it flowed downward through the vertical tubes, and exited at the bottom of the second reaction stage. Salt circulations for both the first and second reaction stages were configured for counter-current flow, with salt entering the bottom of the jacket, flowing upward, and exiting the top of the jacket. Supply temperatures for both the R1 and R2 salt circulations could be independently controlled.

The pilot plant scale reaction system had been utilized in previous experimentation, such that at the time of this study, the R1 and R2 catalysts had been previously operated for about 2,450 hours.

In these studies, the first stage was supplied propylene at a rate of 0.32 kg/hr per tube (0.71 pounds/hr per tube). The feed gas to the reaction system had a nominal propylene concentration of 6% by volume and was operated with a oxygen/propylene volume ratio of 2.07+/−0.02 and a water/propylene volume ratio of 5.15+/−0.10. The product gas stream exiting the second reaction stage was analyzed for propylene and acrolein content to determine conversions. During the study, the R1 salt supply temperature ($T_{R1salt}$) was adjusted to maintain propylene conversion at either 95.5% or 96.5%, depending on the experimental plan; the R2 salt supply temperature ($T_{R2salt}$) was similarly adjusted to maintain the Acrolein conversion at 99.5%. Operating pressure within the reactor was controlled by adjusting a valve on the outlet of the second reaction stage.

Figure 7:
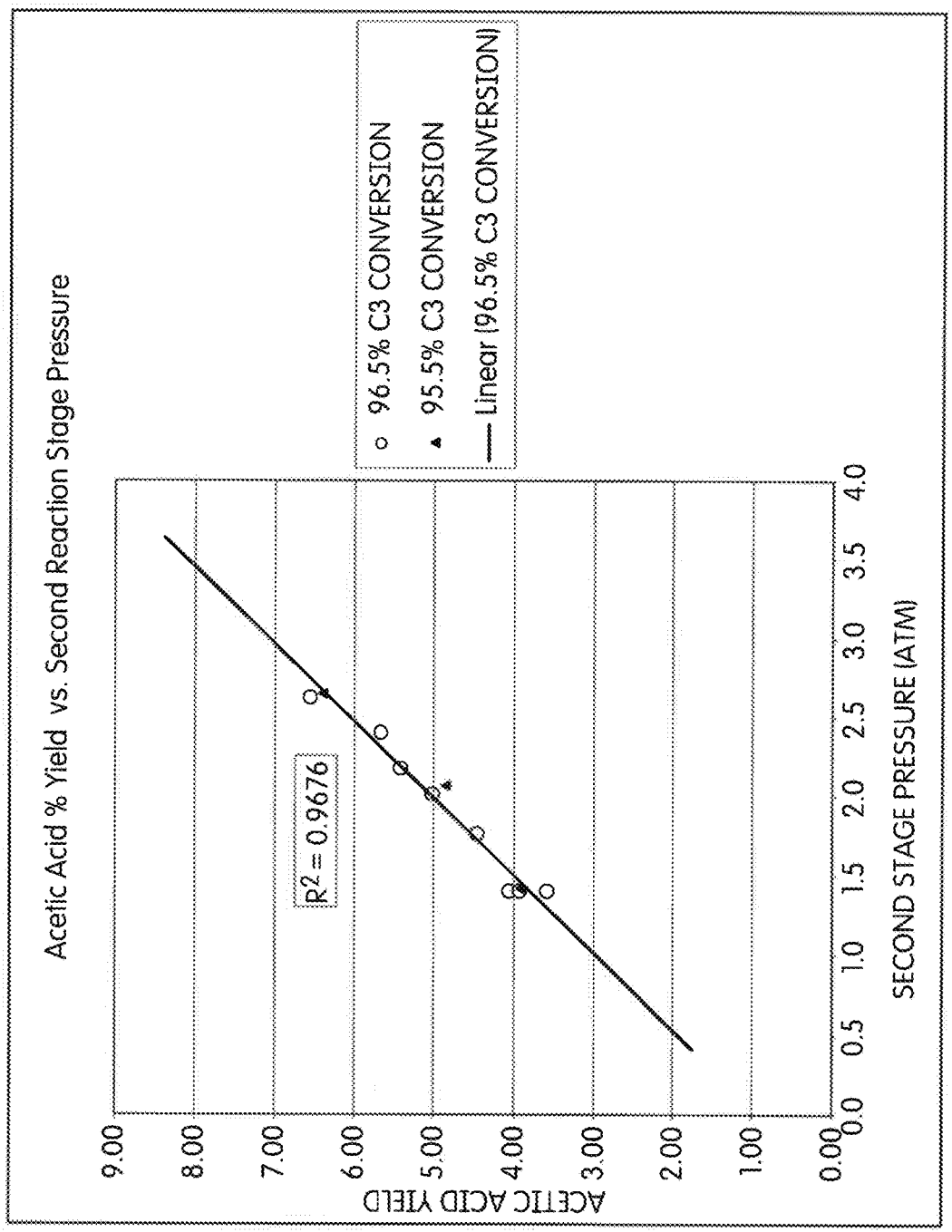
FIG. 7 is a graph showing the relationship of Acetic Acid % yield vs. second reaction stage pressure.

As can be seen from FIG. 7, it was discovered in these experiments that the yield of byproduct acetic acid is highly dependent on the operating pressure within the second reaction stage ($R^2$ value of 0.9676, showing a strong correlation). Because the objective of the propylene oxidation reaction system was to produce acrylic acid, it was preferred to minimize the yield of byproduct acetic acid through operation of the second reaction stage at low pressure.

Example 4—Selection of Tube Size (A) Section 11 of Perry's Chemical Engineers' Handbook (6$^{th}$ ed., 1984) teaches that standard heat exchanger tubes range from 6.35 mm (0.25 in) to 38 mm (1.50 in) in outside diameter and that the wall thickness of heat exchanger tubes is measured in Birmingham wire gauge (BWG) units. Descriptions using this terminology are well known in the art of heat exchanger design, but may not be familiar to those outside of the field. For example, by the description "1 inch×16 BWG heat exchanger tube" is meant a tube with the following dimensions: 25.4 mm (1 in) outside diameter, 1.65 mm (0.065 in) wall thickness, and 22.1 mm (0.87 in) internal diameter. Similarly, the description, a "1.06 in×18 BWG heat exchanger tube" means a tube of 26.9 mm (1.06 in) outside diameter, 1.24 mm (0.049 in) wall thickness, and 24.4 mm (0.962 in) internal diameter. Additionally, the description "1.5 inch×13 BWG heat exchanger tube" means a tube of 38.1 mm (1.5 in) outside diameter, 2.4 mm (0.095 in) wall thickness, and 33.3 mm (1.31 in) internal diameter. Given these examples, it will be evident that the inexact descriptions used in some prior art documents, such as for example the phrase "a one inch tube," can lead to unnecessary confusion; to avoid such issues, actual internal diameters of tubes will therefore be specified in the examples herein.

(B) As a practical matter, the use of heat exchanger tubes greater than about 51 mm (2 in) in outside diameter is very uncommon, given that this is typically the largest seamless tube size routinely stocked by tube manufacturers (sizes larger than about 51 mm are typically considered custom orders with premium pricing and longer delivery).

(C) Further, the commercially-available catalyst pellets that are to be loaded into the reactor tubes are typically a minimum of about 5 to 6 mm in diameter. Thus the range of internal diameters which can be specified for reactor tubes is effectively limited to the range of from about 7 mm to not more than about 50 mm.

(D) It is widely known in the art of propylene oxidation that higher operating temperatures give lower selectivity to acrylic acid and concurrently increased generation of byproducts, such as for example $CO/CO_2$ and acetic acid. It is therefore an object of oxidation reactor design to minimize operating temperatures by effectively balancing the rate of heat removal through the surface area of the tube wall ($Q_r$) against the rate of heat generation from the volume of MMO catalyst within the tube ($Q_g$).

Those of ordinary skill in the art of heat transfer will recognize that $Q_r$ is dependent on the surface area of the tube, A, via the relationship:

$$Q_r = UA(\Delta T)$$

and that the surface area of the tube can be calculated from the geometric relationship:

$$A = 2\pi(r)l$$

where r is the tube radius and l is the length of the tube.

Similarly, $Q_g$ is dependent on the volume of MMO catalyst within the tube, V, which can be calculated from the geometric relationship:

$$V = \pi(r)^2 l$$

where r is again the tube radius and l is the length of the tube.

One of ordinary skill will further recognize that, as tube radius, r, increases, the volume of MMO catalyst within the tube (and therefore the heat generation rate, $Q_g$) increases much more quickly than the surface area of the tube (and hence the heat removal rate, $Q_r$). This relationship [$(r)^2 > (r)$] clearly leads to the conclusion that reaction tubes of small diameter, wherein the heat transfer surface area of the tube wall (A) is large relative to catalyst volume within the tube (V), will be more effective at minimizing operating temperatures than reaction tubes of large diameter.

(E) Additionally, Peters and Timmerhaus (*Plant Design and Economics for Chemical Engineer*, 3$^{rd}$ ed., 1980) teach that "Exchangers with small-diameter tubes are less expensive per square foot of heat-transfer surface than those with large-diameter tubes, because a given surface area can be fitted into a smaller shell diameter . . . ."

Thus, the general consensus of those of ordinary skill in the art of propylene oxidation reactor design was the preferential use of small diameter tubes.

The present inventors have surprisingly discovered that adherence to the common teachings of the art was actually counterproductive. Within the range of tube sizes up to about 50 mm, the present inventors have surprisingly discovered that it is instead preferred to use tubes of larger, rather than smaller, internal diameter within the second reaction stage of the inventive SSOI reactor. Without wishing to be limited by theory, it is believed that the use of larger diameter tubes in the second reaction stage makes it possible to lower the total pressure drop through the catalyst-containing tube, resulting in a substantial reduction in by-product acetic acid formation (see FIG. 7), without changing the total space velocity through the MMO catalyst.

To illustrate this effect, the pressure drop through tubes of different diameters was determined using the following methodology. It is of course possible to collect this data by direct measurement, but such an approach is both time consuming and costly, and it is unnecessary given the calculation method disclosed herein.

The reactor of Example 1, comprising second reaction stage (R2) tubes with an internal diameter of 22.3 mm and a length of 4500 mm, was used to gather the initial process data for this example. The reactor was operated at a total propylene feed rate of 4,745 Nm$^3$/hour (177.1 MSCFH at 60° F./1 atm) with an average feed composition of: 6.5% by volume propylene, 13% by volume oxygen, 31% by volume water, and the balance being inert gases including nitrogen. By direct measurement, reactor pressures within the reactor were found to be:

| | | |
|---|---|---|
| Pressure at inlet of R1 | 2.5 atm | (22.1 psig) |
| Pressure at interstage (=R2 inlet) | 2.0 atm | (15.0 psig) |
| Pressure at outlet of R2 | 1.3 atm | (4.1 psig) |

Based upon the studies of M. Leva, et al. (Bulletin 504, Bureau of Mines, 1951), relationships for pressure drop through spherical catalyst particles within reactor tubes were developed and refined through additional laboratory studies. For tubes of differing geometry, filled with spherical MMO catalyst particles, and operating under the same process conditions (flow, temperature, inlet pressure, and composition), the simplified pressure drop relationship was determined to be:

$$dP = (k)(L/e^3)(1-e)^{1.1}$$

where
dP is the pressure drop through a single tube,
k is a constant tied to process conditions,
L is the length of the tube, and
e is the actual void fraction between catalyst particles within the tube Because void fraction (e) is dependent on the ratio of particle diameter to tube diameter, it must be determined by measurement for each combination of particle diameter and tube size; a significant collection of this data is available in A. Dixon's *Correlations for Wall and Particle Shape Effects on Fixed Bed Bulk Voidage* (Canadian Journal of Chemical Engineering, Vol. 66, October 1988, pp 705-708) and was utilized for this example.

The total volume of the 22,000 reactor tubes with dimensions of 22.3 mm internal diameter and 4500 mm length was 38.65 m$^3$. For each alternative tube diameter considered in the example, this total volume was held constant and the resulting tube length (L) was calculated, as shown in Table 4. Void fractions and pressure drop for each tube size were then determined. Finally, these values were combined with the experimental data of Example 3 to obtain the results summarized in Table 4 below:

TABLE 4

| Tube I.D. | | L | | | dP (psi) R2 inlet- | % Yield Acetic |
|---|---|---|---|---|---|---|
| mm | inches | mm | e | k | outlet | Acid |
| 22.3 | 0.878 | 4,500 | 0.42 | 3.30E−04 | 11.00 calculated measured | 5.1 |
| 12.7 | 0.500 | 13,875 | 0.44 | 3.30E−04 | 28.38 | 7.5 |
| 19.1 | 0.750 | 6,167 | 0.44 | 3.30E−04 | 12.61 | 5.3 |

TABLE 4-continued

| Tube I.D. | | L | | | dP (psi) R2 inlet- | % Yield Acetic |
|---|---|---|---|---|---|---|
| mm | inches | mm | e | k | outlet | Acid |
| 23.6 | 0.929 | 3,844 | 0.42 | 3.30E−04 | 9.40 | 4.8 |
| 25.4 | 1.000 | 3,469 | 0.42 | 3.30E−04 | 8.48 | 4.7 |
| 31.8 | 1.250 | 2,220 | 0.40 | 3.30E−04 | 6.52 | 4.4 |
| 38.1 | 1.500 | 1,542 | 0.40 | 3.30E−04 | 4.20 | 4.1 |

It was clear from this example that tubes greater than the base 22.3 mm internal diameter provide lower amounts of byproduct acetic acid, while that tubes smaller than the base 22.3 mm internal diameter provide higher amounts of byproduct acetic acid. Further, it is evident from the experimental data that a beneficial reduction in by-product acetic acid production may be achieved even with relatively minor changes in tube internal diameter. Additionally, because the inventive SSOI reactor design resisted the accumulation of carbonaceous foulants, the pressure drop across the reactor, and therefore the operating pressure of the second reaction stage, did not change significantly over time; as a result, the pressure-reducing benefit of increased second reaction stage tube diameter was realized over the entire life of the catalyst charge—and not just the first few months of operation.

Example 5—Tube Count

Another approach to minimization of pressure within the second reaction stage is to reduce the overall tube length while simultaneously increasing the total number of tubes (also known as "tube count") within the reactor. This design optimization may be utilized without changing tube internal diameter or the total volume of each reaction stage. Although reactor shell diameter, and therefore fabrication cost, increases with increasing tube count, it may at times be advantageous to incur this additional capital cost in order to achieve reduced pressure drop and the associated reduction in acetic acid yield. Such economic assessments are within the ability of one of ordinary skill in the art of process design, given the benefit of the present disclosure.

Table 5A illustrates how the length of each tube occupied by catalyst and the tube count may be varied in the design of a SSOI reactor, while maintaining a fixed tube internal diameter of 22.3 mm and a fixed reaction stage volume within the reactor.

TABLE 5A

SSOI Reactor Design Options
120 kT/year Acrylic Acid Basis (7 mole % propylene feed concentration)
R1 Tube I.D. = R2 Tube I.D. = 22.3 mm
Total Available Volume in first reaction stage = 52.3 m$^3$
Total Available Volume in second reaction stage = 46.2 m$^3$

| | | | | |
|---|---|---|---|---|
| Length Occupied by R1 Catalyst | 4600 mm | 4100 mm | 3500 mm | 3000 mm |
| Length Occupied by R2 Catalyst | 4000 mm | 3600 mm | 3100 mm | 2700 mm |
| Tube Count (R1 and R2 are equal) | 29,410 | 32,673 | 38,057 | 44,653 |

Table 5B illustrates how the length of each tube occupied by catalyst and the tube count may be varied in the design of a SSOI reactor, while maintaining a fixed tube internal diameter of 25.4 mm and a fixed reaction stage volume within the reactor.

TABLE 5B

SSOI Reactor Design Options
120 kT/year Acrylic Acid Basis (7 mole % propylene feed concentration)
R1 Tube I.D. = R2 Tube I.D. = 25.4 mm
Total Available Volume in first reaction stage = 52.3 m³
Total Available Volume in second reaction stage = 46.2 m³

| | | | | |
|---|---|---|---|---|
| Length Occupied by R1 Catalyst | 3000 mm | 3500 mm | 4600 mm | 4690 mm |
| Length Occupied by R2 Catalyst | 2700 mm | 3100 mm | 4000 mm | 4140 mm |
| Tube Count (R1 and R2 are equal) | 34,419 | 29,334 | 22,669 | 22,000 |

Table 5C illustrates how the length of each tube occupied by catalyst and the tube count may be varied in the design of a SSOI reactor with a fixed reaction stage volume; this table also demonstrates that an equivalent change in catalyst length produces the same percent increase in tube count, regardless of the internal diameter of the tube.

TABLE 5C

SSOI Reactor Design Options
120 kT/year Acrylic Acid Basis (8 mole % propylene feed concentration)
R1 Tube I.D. = R2 Tube I.D.
Total Available Volume in first reaction stage = 53.7 m³
Total Available Volume in second reaction stage = 44.5 m³

| Tube I.D. | 25.4 mm (1") | | 31.75 mm (1.25") | | 38.1 mm (1.5") | |
|---|---|---|---|---|---|---|
| Length Occupied by R1 Catalyst, mm | 3500 | 3000 | 3500 | 3000 | 3500 | 3000 |
| Length Occupied by R2 Catalyst, mm | 2900 | 2500 | 2900 | 2500 | 2900 | 2500 |
| Tube Count (R1 and R2 are equal) | 30,310 | 35,360 | 19,398 | 22,630 | 13,471 | 15,716 |
| Increase in tube count | 16.7% | | 16.7% | | 16.7% | |

Example 6—Catalyst Mass Ratio

The following example is exceptional in the art due to both the long duration of the individual experiments as well as the large number of commercial-scale trials performed. In this example, a series of catalyst evaluations were performed using commercial-scale SSOI-type propylene oxidation reactors, comprising between 15,000 and 25,000 tubes each. In each reactor, there were an equal number of tubes in both the first (R1) reaction stage and the second (R2) reaction stage and all of the tubes were of 22.3 mm (0.878 inch) internal diameter.

For each experimental trial, all of the reaction tubes within a given reactor were filled with an equal mass of catalyst and any void space in the tube ends was filled with sufficient 6.4 mm (0.25") EnviroStone 66 ceramic spheres to achieve a uniform pressure drop through each tube.

Consistent with at least one embodiment of the present disclosure, the interstage cooling section of each reactor was fitted with high-void fraction (at least 90% void fraction) turbulence-enhancing insets, the open interstage region was loaded with 1.5" diameter high surface area EnviroStone 66 ceramic spheres, and the combined process gas residence time within the interstage cooler and the open interstage region (herein referred to as the "interstage residence time") was constrained to not more than 3.0 seconds.

During the trials, each tube within the test reactor was supplied propylene at an average flow rate of between 0.16 to 0.21 Nm³/hour (6 and 8 SCFH at 60 F/1 atm) per tube. Feed gas composition to each reactor was controlled at an average of 7+/−0.5% propylene, a steam:propylene volume ratio of about 3.6+/−2, and an oxygen:propylene volume ratio of about 1.8+/−1.

All reactors were cooled with circulating streams of HITEC salt. At the beginning of operation, the cooling salt for the first reaction stage was initially supplied at a temperature, $T_{R1salt}$, of about 315° C. (600° F.) and the cooling salt for the second reaction stage was initially supplied at a temperature, $T_{R2salt}$, of about 265° C. (510° F.).

The composition of the gas stream exiting the second reaction stage of each reactor, herein referred to as the "reactor product gas" stream, was monitored using online gas chromatograph analyzers. Specific measurements included the concentration of unreacted propylene and the concentration of unreacted acrolein remaining in the product gas.

Throughout the period of experimental operation, $T_{R1salt}$ (first stage salt supply temperature) was adjusted to maintain the unreacted propylene concentration in the product gas at between 0.13-0.26 mol %, and $T_{R2salt}$ (second stage salt supply temperature) was adjusted to maintain the unreacted acrolein concentration in the product gas at about 300 ppm. Additionally, the temperature of the cooling salt supplied to the interstage heat exchanger ($T_{ISHXsalt}$) was adjusted to maintain the temperature of the process gas entering the open interstage region at a value of between about 240° C. and 280° C.

Over long periods of operation, catalyst aging made it necessary to gradually increase $T_{R1salt}$ and $T_{R2salt}$ in order to maintain the yield of acrylic acid from the reactor. Eventually, however, catalyst operating temperatures reached a maximum value and further increases in either $T_{R1salt}$ or $T_{R2salt}$ became ineffective at improving acrylic acid yield. At this point, the catalyst had reached the end of its useful life and needed to be replaced. Generally, these final values of $T_{R1salt}$ and $T_{R2salt}$ were about 355° C. (670° F.) and about 295° C. (560° F.), respectively.

TABLE 6

| Trial # | Catalyst Used | | Catalyst Mass per Tube (kg) | | Catalyst Mass Ratio | Catalyst Useful Life (years) | |
|---|---|---|---|---|---|---|---|
| | R1 | R2 | R1 | R2 | R2:R1 | R1 | R2 |
| 1a & b | YX-38 | T-202 | 1.499 | 1.414 | 0.94 | 4.88 | 2.71 * & 2.18 |
| 2a & b | ACF-2 | ACS-2 | 1.499 | 1.414 | 0.94 | 4.19 | 2.28 * & 1.91 |
| 3 | ACF-2 | ACS-2 | 1.529 | 1.963 | 1.28 | 4.14 | 4.14 |
| 4a & b | ACF-4 | ACS-6 | 1.499 | 1.414 | 0.94 | 4.01 | 2.08 * & 1.93 |
| 5 | ACF-4 | ACS-6 | 1.325 | 1.962 | 1.48 | 4.15 | 4.15 |
| 6a &b | ACF-7 | ACS-7 | 1.273 | 1.338 | 1.05 | 4.42 | 3.52 * & 0.90 |
| 7 | ACF-7 | ACS-7 | 1.295 | 1.886 | 1.46 | 4.71 | 4.71 |
| 8 | ACF-7 | ACS-7 | 1.295 | 2.122 | 1.64 | 3.73 | 3.73+ |

\* = R2-only catalyst change ("partial repack")
+ = reduced $T_{R2salt}$ rate of increase vs. other trials; R2 useful life > R1

As shown in Table 6, trials 1, 2, 4, and 6 all required partial R2 catalyst repacks; that is, the useful life of the R2 catalyst charge was roughly half that of the R1 catalyst charge, making it necessary to replace the R2 catalyst well before the R1 catalyst required replacement. In trial 8, the useful life of the R2 catalyst charge exceeded that of the R1 charge. However, in trials 3, 5, and 7, the useful life of the R1 and the R2 catalyst charges were effectively matched, eliminating the need for a partial repack. These experiments showed that, for the SSOI reactor design of at least one embodiment of the present invention, it was possible to operate with matched first stage and second stage catalyst lifetimes when the catalyst mass Ratio (kg of first stage catalyst/kg second stage catalyst) was between about 1.25 and about 1.60. At catalyst mass ratios of less than about 0.95, the useful life of the R2 catalyst was substantially shorter than that of the R1 catalyst. At catalyst mass ratios of more than about 1.60, such as in the case of trial 8, the useful life of the R2 catalyst was longer than that of the R1 catalyst. Furthermore, the data suggested that at catalyst mass ratios substantially higher than about 1.65, for example at a ratio of 1.80, or even 2.0, the useful life of the R2 catalyst could be expected to be significantly longer than that of the R1 catalyst, thereby requiring early replacement of the R1 catalyst. It was especially surprising to find that this discovery applied to many different commercial catalyst types, including catalysts from more than one supplier. Reactor operation with matched catalyst lifetimes provided significant economic benefit by eliminating partial repacks without incurring additional costs for the installation of excessive amounts of catalyst. It was concluded that the amount of catalyst loaded into the tubes of the SSOI reactor of certain embodiments can be controlled to achieve a catalyst mass ratio (kg of first stage catalyst/kg second stage catalyst) of not less than about 0.95 and not more than about 1.65 such as, for example, between about 1.25 and about 1.60

Example 7—Supplemental Oxidant Addition/Residence Time

The previously-described reactor embodiment of FIG. 4 had 22,000 tubes and was operated with supplemental oxidant addition to achieve an acrylic acid nameplate capacity of 110 kT per year. It was desired to determine the interstage residence time, as well as the residence time of the process gas flow through the interstage heat exchanger tubes (the ISHX residence time) at design operating rates.

As previously indicated in Table 7A (Case 2), the reactor embodiment of FIG. 4 was designed for operation at a propylene feed rate of 21,344 pph (9,702 kg/hr), a propylene:air volume ratio of 0.122, and a steam:air volume ratio of 0.367. As measured at the reference conditions of 240° C. and 30 psia (2 atm), the total gas flow entering the interstage region was about 2,187,662 ft$^3$/hr (61,956 m$^3$/hr).

TABLE 7B

Residence Time within Interstage Heat Exchanger (ISHX) Tubes
22.3 mm I.D. (0.878 in) × 2100 mm (6.9 ft) × 22,000 tubes;
one turbulence inducing twistee insert inserted into each tube

| | | |
|---|---|---|
| Total Volume of empty ISHX Tubes | 638 ft$^3$ | 18.1 m$^3$ |
| Void fraction of Twistee inserts within ISHX Tubes | 0.923 | |
| Available Volume in ISHX Tubes, after deducting volume of inserts | 589 ft$^3$ | 16.7 m$^3$ |
| Effective Space Velocity through ISHX = (2,187,662 ft$^3$/hr)/(589 ft$^3$) | 3,715 hr$^{-1}$ | |
| Equivalent residence time within the ISHX | 0.969 seconds | |

This result of 0.969 seconds was fully consistent with the targeted embodiment of a residence time of process gas through the Interstage Heat Exchanger not more than 1.5 seconds.

TABLE 7C

Residence Time within Open Interstage Region
152 mm (0.5 ft) tall × 5517 mm (18.1 ft) in diameter;
volume is completely filled with 20 ppi (pores-per-inch) ceramic foam

| | | |
|---|---|---|
| Total Volume of empty Interstage Region | 129 ft$^3$ | 3.64 m$^3$ |
| Void fraction of ceramic foam | 0.92 | |
| Available Volume in Interstage Region, after deducting volume occupied by solid portion of ceramic foam | 118 ft$^3$ | 3.35 m$^3$ |
| Effective Space Velocity through Open Interstage Region = (2,187,662 ft$^3$/hr)/(118 ft$^3$) | 18,492 hr$^{-1}$ | |
| Equivalent residence time upstream of mixer within the Open Interstage Region | 0.195 seconds | |

TABLE 7D

Residence Time - Mixer Inlet Contracting Section

| | | |
|---|---|---|
| Total Volume of empty Contracting Section | 135.4 ft$^3$ | 3.8 m$^3$ |
| Effective Space Velocity through Contracting Section = (2,284,360 ft$^3$/hr)/(784.3 ft$^3$) | 16,158 hr$^{-1}$ | |
| Equivalent residence time within the Contracting Section | 0.223 seconds | |

At the intermediate throat section of the mixer, the total volumetric flow increased due to the addition of the supplemental oxidant feed. As measured at the reference conditions of 240° C. and 30 psia (2 atm), the total gas flow passing through the intermediate throat section and the outlet expanding section increased to about 2,408,820 ft$^3$/hr (68,220 m$^3$/hr).

TABLE 7E

Residence Time - Mixer Throat & Expansion

| | | |
|---|---|---|
| Total Volume of empty Intermediate Throat Section | 18.9 ft$^3$ | 0.5 m$^3$ |
| Total Volume of empty Outlet Expanding Section | 767.8 ft$^3$ | 21.7 m$^3$ |
| Effective Space Velocity through Throat Section = (2,408,820 ft$^3$/hr)/(18.9 ft$^3$) | 127,792 hr$^{-1}$ | |
| Effective Space Velocity through Expanding Section = (2,408,820 ft$^3$/hr)/(767.8 ft$^3$) | 3,137 hr$^{-1}$ | |
| Combined residence time within the Throat and Expanding Sections of mixer | 1.176 seconds | |

In accordance with the definition of the previous examples, the interstage residence time for this embodiment was the sum total of the residence time through the interstage heat exchanger, the ceramic foam, and each section of the venturi-mixer. Therefore, combining the results from Tables 7B through 7E, it was determined that the interstage residence time was 2.56 seconds. This result was consistent with the targeted interstage residence time of not more than 3 seconds.

What is claimed is:

1. An upflow single shell open interstage reactor comprising:
    a) a first shell-and-tube reaction stage comprising a plurality of reaction tubes, wherein the reaction tubes of the first reaction stage comprise a first catalyst;
    b) an interstage heat exchanger;
    c) an open interstage region; and
    d) a second shell-and-tube reaction stage comprising a plurality of reaction tubes, wherein the reaction tubes of the second reaction stage comprise a second catalyst;
    wherein said interstage heat exchanger is positioned between said first reaction stage and said open interstage region, and
    wherein said reactor is configured for upflow operation.

2. The reactor of claim 1, wherein said interstage heat exchanger is a shell-and-tube heat exchanger and comprises a plurality of interstage heat exchanger tubes.

3. The reactor of claim 2, wherein said interstage heat exchanger tubes are coaxially continuous with the reaction tubes of the first reaction stage.

4. The reactor of claim 2, wherein said interstage heat exchanger tubes comprise a catalyst retaining device.

5. The reactor of claim 4, wherein said catalyst retaining device is capable of inducing turbulence within the said interstage heat exchanger tubes.

6. The reactor of claim 2, wherein said interstage heat exchanger tubes comprise high void fraction, turbulence-inducing inserts.

7. The reactor of claim 6, wherein said inserts have a void fraction of at least 85%.

8. The reactor of claim 1, wherein said first reaction stage further comprises a first shellside coolant and said second reaction stage further comprises a second shellside coolant.

9. The reactor of claim 8, wherein said first shellside coolant is controlled independently of said second shellside coolant.

10. The reactor of claim 2, wherein said interstage heat exchanger further comprises a shellside heat exchanger coolant.

11. The reactor of claim 10, wherein said first reaction stage further comprises a first shellside coolant that is controlled independently of said heat exchanger coolant.

12. The reactor of claim 1, wherein said open interstage region is at least partially filled with at least one inert material.

13. The reactor of claim 12, wherein said inert material has a surface area to bulk volume ratio of at least 78.7 m$^2$/cubic m (24 ft$^2$/cubic foot).

14. The reactor of claim 12, wherein said inert material is present in an amount sufficient to provide at least 2790 m$^2$ (30,000 ft$^2$) of total surface area.

15. The reactor of claim 1, wherein the reaction tubes of the first reaction stage have a different cross-sectional area than the reaction tubes of the second reaction stage.

16. The reactor of claim 15, wherein the reaction tubes of the second reaction stage have a cross-sectional area at least 25% greater than the cross-sectional area of the reaction tubes of the first reaction stage.

17. The reactor of claim 16, wherein the reaction tubes of the second reaction stage have a cross-sectional area at least 50% greater than the cross-sectional area of the reaction tubes of the first reaction stage.

18. The reactor of claim 1, wherein the reaction tubes of the second reaction stage have an internal diameter greater than 22.3 mm (0.878 in).

19. The reactor of claim 18, wherein the reaction tubes of the second reaction stage have an internal diameter greater than 25.4 mm (1 in).

20. The reactor of claim 1, wherein said open interstage region comprises a supplemental oxidant supply line.

21. The reactor of claim 20, wherein said open interstage region further comprises a supplemental oxidant mixing assembly.

22. The reactor of claim 21, wherein said supplemental oxidant mixing assembly comprises a venturi mixer.

23. The reactor of claim 20, wherein said supplemental oxidant supply line comprises an oxidant heat exchanger.

24. The reactor of claim 1, further comprising inlet and outlet reactor heads, wherein at least one of said inlet reactor head and said outlet reactor head is removable.

25. The reactor of claim 1, wherein at least one region chosen from the first reaction stage, the interstage heat exchanger, and the second reaction stage is configured for co-current coolant circulation.

26. The reactor of claim 1, wherein at least one region chosen from the first reaction stage, the interstage heat exchanger, and the second reaction stage is configured for counter-current coolant circulation.

27. The reactor of claim 1, wherein the second reaction stage comprises at least 22,000 reaction tubes.

28. The reactor of claim 27, wherein the second reaction stage comprises at least 30,000 reaction tubes.

29. The reactor of claim 1, wherein the number of reaction tubes in the first reaction stage is approximately equal to the number of reaction tubes in the second reaction stage.

30. The reactor of claim 1, wherein the number of reaction tubes in the first reaction stage is different than the number of reaction tubes in the second reaction stage.

31. The reactor of claim 1, wherein the reaction tubes in the second reaction stage are no greater than 4,500 mm (177 in) in length.

32. The reactor of claim 1, wherein said interstage heat exchanger is capable of maintaining a process gas leaving the interstage heat exchanger at a temperature ranging from 240° C. to 280° C.

33. The reactor of claim 1, wherein the reaction tubes of the first reaction stage have an internal diameter greater than 22.3 mm.

* * * * *